United States Patent
McGuckin, Jr. et al.

(10) Patent No.: US 6,572,630 B1
(45) Date of Patent: Jun. 3, 2003

(54) ATHERECTOMY DEVICE

(75) Inventors: James F. McGuckin, Jr., Radnor, PA (US); Peter W. J. Hinchliffe, Downington, PA (US); Walter H. Peters, Downington, PA (US)

(73) Assignee: Rex Medical, L.P, Conshohocken, PA (US)

( * ) Notice: Subject to any disclaimer, the term of this patent is extended or adjusted under 35 U.S.C. 154(b) by 255 days.

(21) Appl. No.: 09/629,313

(22) Filed: Jul. 31, 2000

Related U.S. Application Data

(63) Continuation-in-part of application No. 29/117,719, filed on Jan. 31, 2000, now abandoned.

(51) Int. Cl.⁷ .............................................. A61B 17/22
(52) U.S. Cl. ...................................................... 606/159
(58) Field of Search .......................... 606/80, 79, 170, 606/159

(56) References Cited

U.S. PATENT DOCUMENTS

| | | | |
|---|---|---|---|
| 4,038,985 A | * 8/1977 | Chiulli | 606/159 |
| 4,445,509 A | * 5/1984 | Auth | 600/565 |
| 4,646,736 A | 3/1987 | Auth | |
| 4,664,112 A | 5/1987 | Kensey et al. | |
| 4,990,134 A | 2/1991 | Auth | |
| 5,019,088 A | 5/1991 | Farr | |
| 5,100,426 A | 3/1992 | Nixon | |
| 5,217,474 A | 6/1993 | Zacca et al. | |
| 5,267,955 A | 12/1993 | Hanson | |
| 5,308,354 A | * 5/1994 | Zacca et al. | 606/159 |
| 5,318,576 A | 6/1994 | Plassche, Jr. et al. | |
| 5,411,478 A | * 5/1995 | Stillabower | 604/103.08 |
| 5,489,291 A | 2/1996 | Wiley | |
| 5,507,761 A | 4/1996 | Duer | |
| 5,556,405 A | * 9/1996 | Lary | 606/159 |
| 5,584,843 A | 12/1996 | Wulfman et al. | |
| 5,616,149 A | * 4/1997 | Barath | 604/103.07 |
| 5,632,755 A | 5/1997 | Nordgren et al. | |
| D381,474 S | 7/1997 | Kapec et al. | |
| 5,649,941 A | * 7/1997 | Lary | 604/22 |
| 5,681,336 A | 10/1997 | Clement et al. | |
| D390,955 S | 2/1998 | Sjostrom et al. | |
| 5,766,192 A | * 6/1998 | Zacca | 606/159 |
| 5,873,905 A | * 2/1999 | Plaia et al. | 606/194 |
| 5,897,566 A | 4/1999 | Shturman et al. | |
| 5,938,670 A | 8/1999 | Keith et al. | |
| 6,007,533 A | 12/1999 | Casscells et al. | |
| 6,015,420 A | 1/2000 | Wulfman et al. | |
| 6,080,170 A | 6/2000 | Nash et al. | |
| 6,080,171 A | * 6/2000 | Keith et al. | 606/159 |
| 6,096,054 A | 8/2000 | Wyzgala et al. | |
| 6,146,395 A | * 11/2000 | Kanz et al. | 606/159 |
| 6,156,048 A | * 12/2000 | Wulfman et al. | 606/159 |
| 6,165,187 A | 12/2000 | Reger | |
| 6,183,487 B1 | * 2/2001 | Barry et al. | 606/159 |
| 6,206,898 B1 | 3/2001 | Honeycutt et al. | |
| 6,416,526 B1 | 7/2002 | Wyzgala et al. | |

FOREIGN PATENT DOCUMENTS

| | | |
|---|---|---|
| DE | 19639193 | 4/1998 |
| WO | 9612453 | 5/1996 |
| WO | 9838928 | 9/1998 |

OTHER PUBLICATIONS

Medi–tech Boston Scientific Brochure, Rotatablator* Rotational Angioplasty System brochure, 1997.

* cited by examiner

Primary Examiner—Michael J. Milano
Assistant Examiner—P Roberts
(74) Attorney, Agent, or Firm—Neil D. Gershon

(57) ABSTRACT

Atherectomy device for removing plaque from the interior of a lumen comprising a rotatable head having a nose, central portion and tail portion. The nose position is bulbously outwardly curved, the tail portion defines a rear extremity of the head and is rectangular in transverse cross-section and tapered, and the central portion tapers from the circular nose portion to the tail portion.

19 Claims, 24 Drawing Sheets

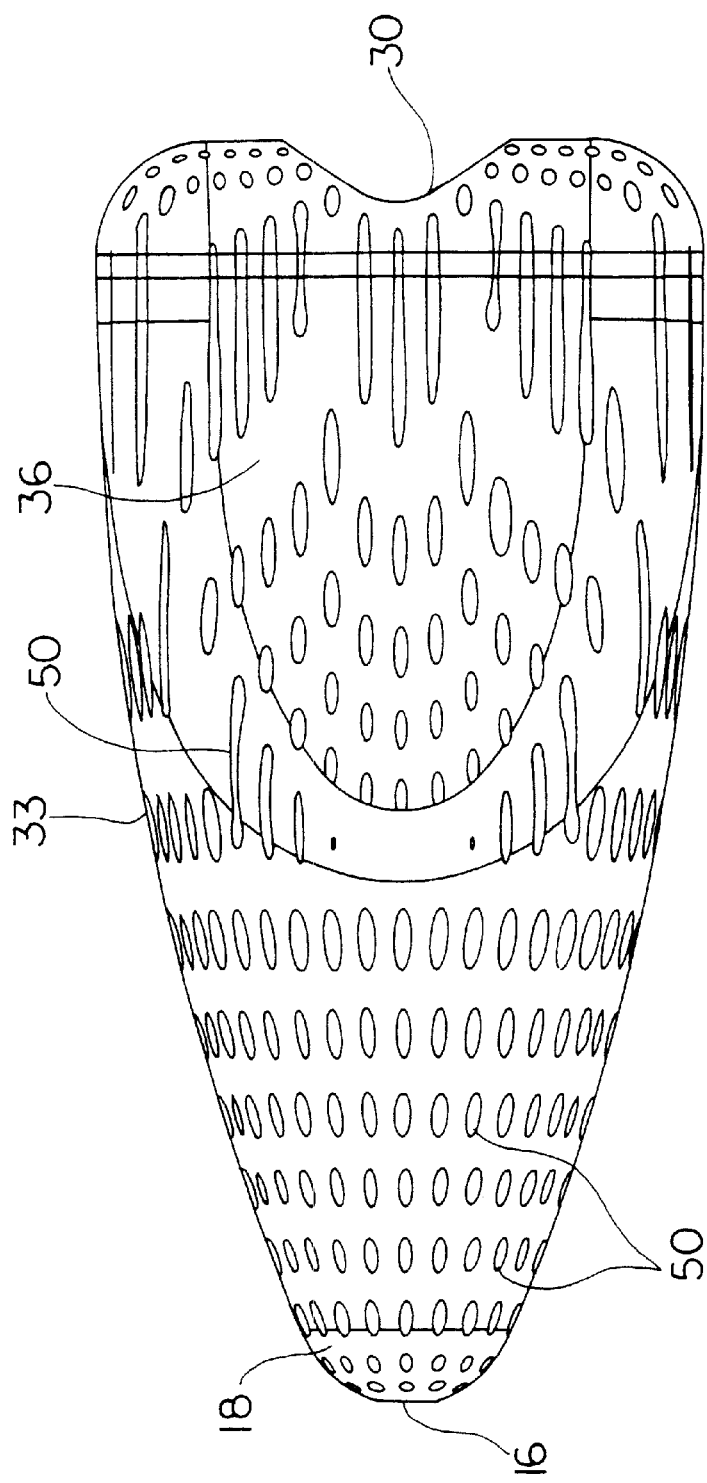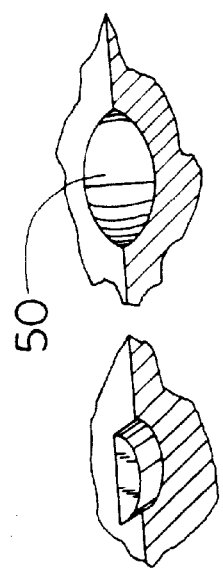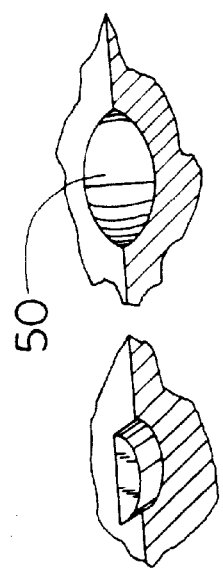
FIG. 14-1  FIG. 14-2  FIG. 14-3

ATHERECTOMY DEVICE

CROSS-REFERENCE TO RELATED PATENT APPLICATION

This patent application is a continuation in part of U.S. Design Pat. application Ser. No. 29/117,719 filed Jan. 31, 2000 in the names of James F. McGuckin, Jr., Peter W. Hinchliffe and Walter H. Peters.

BACKGROUND OF THE INVENTION

This invention relates to methods and apparatus for mechanical removal of plaque and thrombolytic material from the interior of veins and arteries in the human body.

Apparatus for mechanical removal of plaque and thrombolitic material from the interior veins and arteries in the human body is disclosed in U.S. Pat. No. 4,990,134.

SUMMARY OF THE INVENTION

In one of its aspects, this invention provides an atherectomy device for removing plaque from the interior of the lumen upon travel of the device therethrough where the device includes a rotatable head having nose, central and tail portions. The nose portion is preferably bulbously curved outwardly and defines a forward extremity of the head for initial passage within the lumen. The nose portion is preferably of circular shape at juncture with a central portion with the center of the circular shape being coincident with a longitudinal passageway extending through the head.

The tail portion is preferably separated from the nose portion by the central portion and defines a rear extremity of the head as the head portion passes through the lumen. The tail portion is preferably of rectangular transverse cross-section and tapers from a relatively smaller maximum diameter at juncture with the central portion to a relatively larger maximum diameter at a rear extremity of the rotatable head.

The central portion preferably transitionally tapers from and connects the circular central portion to the rectangular transverse cross-section tail portion with the central portion preferably being of larger transverse cross-sectional area at juncture with a tail portion than at juncture with the nose portion.

The head preferably has a plurality of longitudinally extending cutting grooves formed therein commencing proximate juncture of the circular nose portion and the central portion, with the cutting grooves extending rearwardly therefrom.

The head preferably further includes a central passageway extending the longitudinal length thereof coincidentally with the longitudinal axis of the head and adapted for passage therethrough of wire means for guiding travel of the head through the lumen.

At least some of the cutting grooves in the surface of the head preferably extend along the central portion and the rear portion.

The passageway through the head preferably includes an enlarged portion at the rear end of the head for securement to the head of means for rotating the head.

The cutting grooves preferably extend along the surface of the non-tapering sides of the rectangular cross-section of the tail portion.

The cutting grooves preferably transition longitudinally from V-shapes to rectangular shapes.

DESCRIPTION OF THE DRAWINGS

FIG. 14-1 is a top view of the embodiment of the athrectomy device illustrated in FIG. 13.

FIG. 14-2 is an enlarged broken view of a cutting surface depression alternative to the athrectomy device of FIG. 14-1.

FIG. 14-3 is a partially broken section view of a cutting surface dimple alternative to the surface cutting depression illustrated in FIG. 14-2.

DETAILED DESCRIPTION OF THE INVENTION

Figure 1:
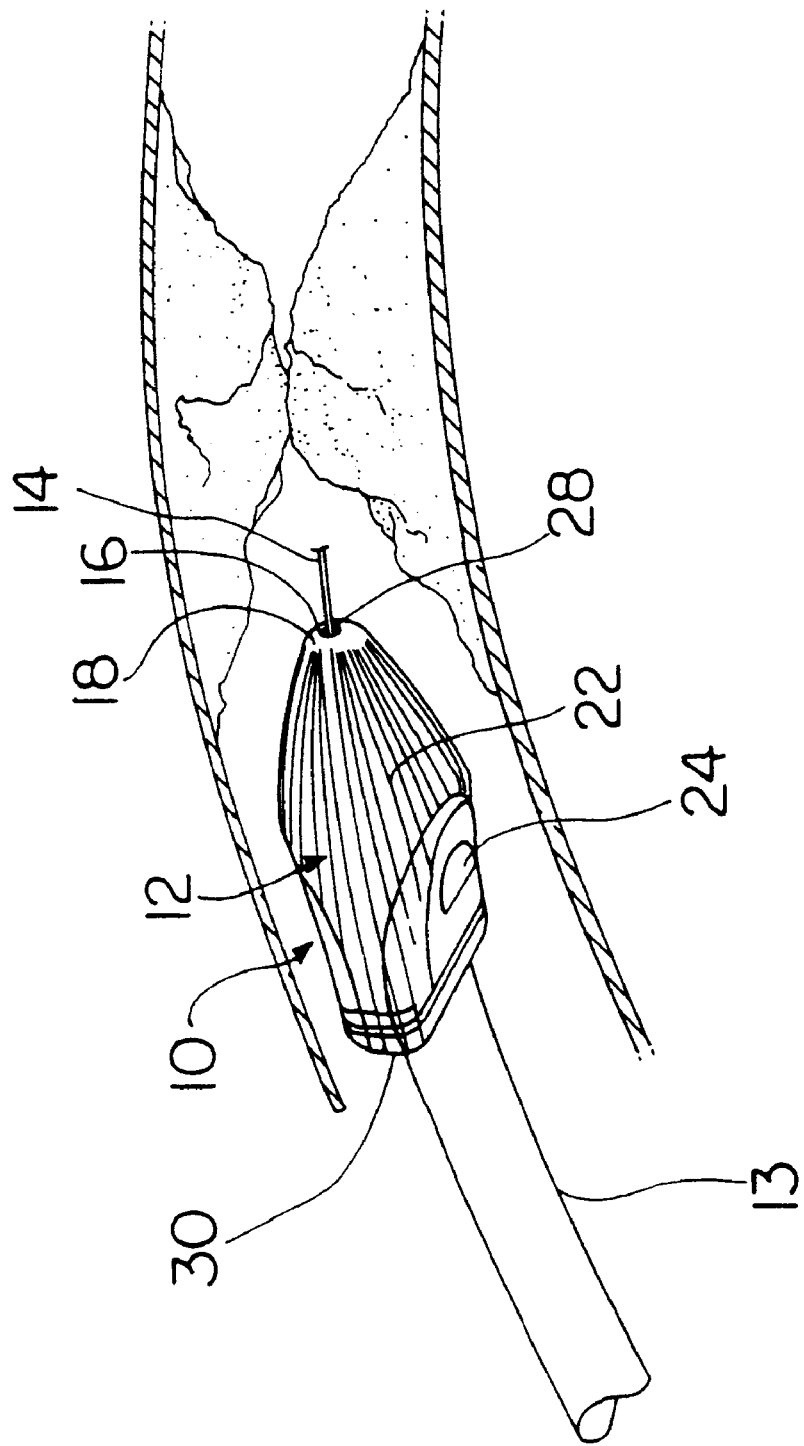
FIG. 1 is an isometric depiction of the preferred embodiment of an atherectomy device in accordance with the invention shown within a body lumen in proximity to plaque deposits to be removed from the lumen interior by the atherectomy device.

Referring to the drawings, there is shown in FIG. 1 an illustration of one embodiment of an atherectomy device designated generally 10 for mechanical removal of plaque and thrombolytic material from the interior of veins and arteries in the human body. In one aspect of the invention, the atherectomy device 10 includes a rotatable head 12, wherein the rotatable head 12 rotates to remove plaque, thrombus and other residue material from the interior of body lumens, notably veins and arteries. Passage through the lumen is facilitated by use of a guide wire 14 extending beyond the front end of the rotatable head 12. Guide wire 14 is positioned within the body lumen prior to introduction of athrectomy device 10 in the lumen. Guide wire 14 serves to position and guide the athrectomy device as it passes through the lumen. Accordingly, guide wire 14 resides slidably within and passes entirely through a central longitudinally extending passageway 28 formed in rotatable head 12 and out the tail or rear end 30 of rotatable head 12.

Figure 2:
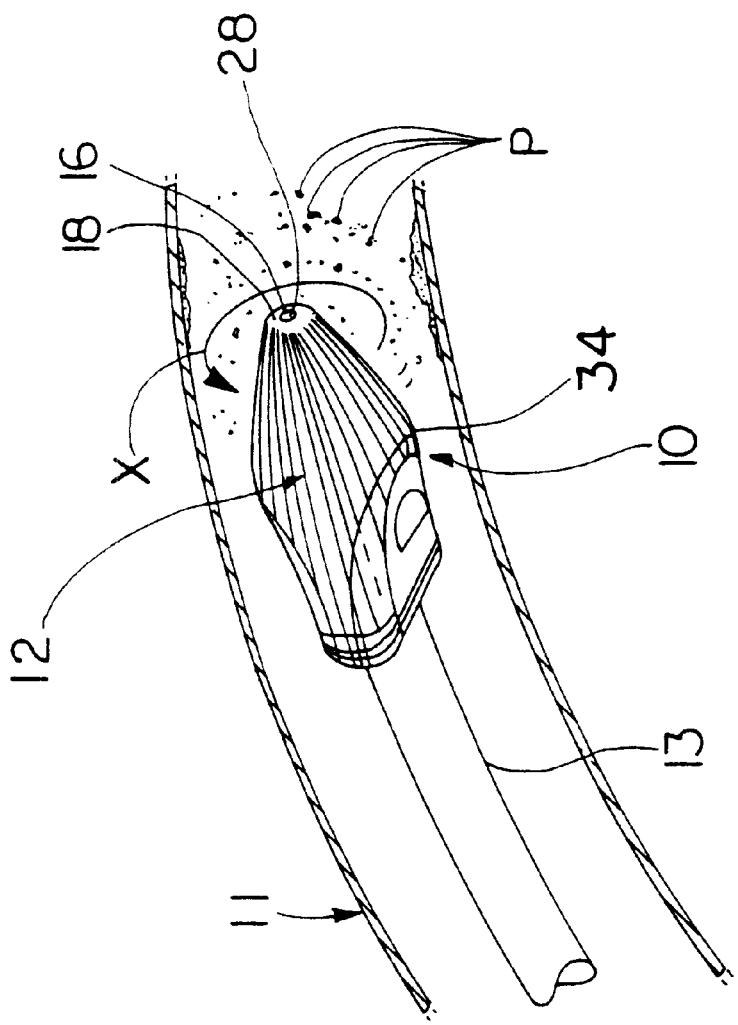
FIG. 2 is an isometric depiction of an atherectomy device in accordance with the invention as shown in FIG. 1 within a body lumen, removing plaque deposits from the lumen interior.
Figure 3:
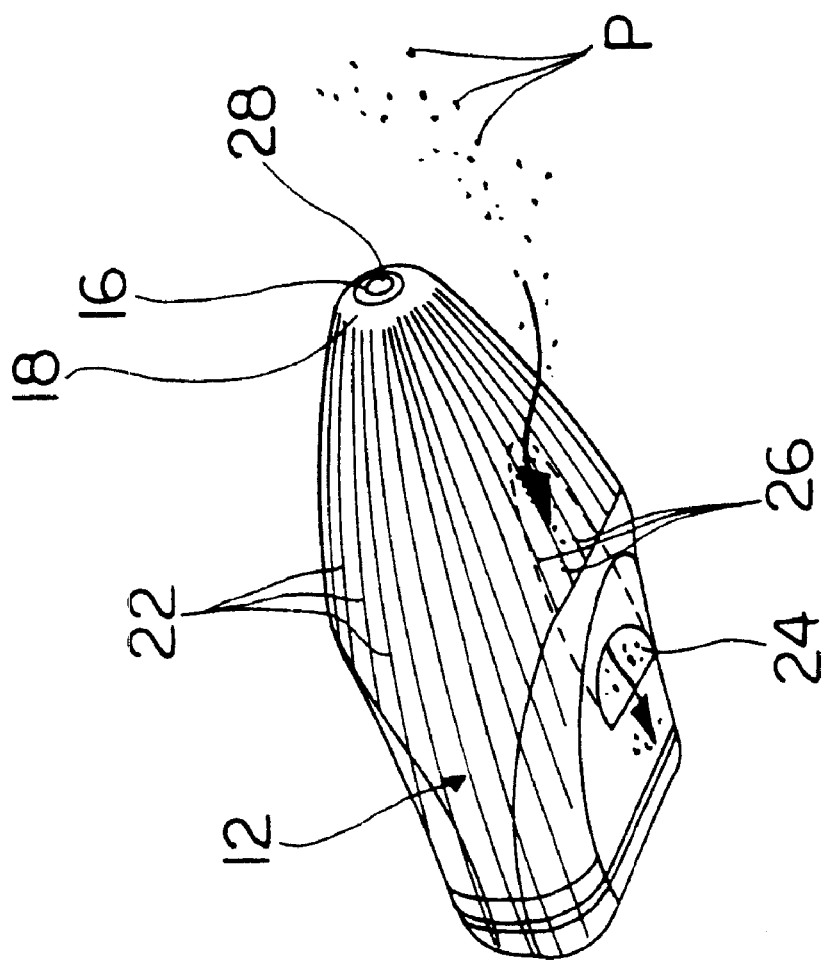
FIG. 3 is an isometric depiction of an atherectomy device in accordance with the invention as shown in FIGS. 1 and 2, with particles of plaque which have been removed from the lumen interior illustrated passing by and through the atherectomy device.

Rotatable head 12 is shown rotating as rotatable head 12 travels axially or longitudinally through the lumen in FIG. 2. Arrow X indicates the direction of rotation of rotatable head 12 as rotatable head 12 moves longitudinally along the lumen; loose particles designated P indicate the breakdown of plaque from within the lumen.

As apparent from the drawings, the atherectomy head 12 preferably is not of circular cross section over its entire longitudinal length. The high points of rotatable head 12 are points of relative maximum radial displacement from the axis of rotation of head 12, which is coincident with a longitudinal passageway extending the length of atherectomy head 12. These high points on what amounts to an oval shaped cross section of head 12 at a central transition 34 are what contact the interior walls of the lumen. Speed of rotation of rotatable head 12 is preferably in the neighborhood of about 120,000 revolutions per minute. Atherectomy head 12 may be injection molded steel or ceramic material. Plastics are also within the purview of the invention but steel or ceramic is preferable from the standpoint of wear resistance.

Head 12 has a nose portion 18 which is bulbously outwardly curved and defines a forward extremity of head 12 for initial passage within the lumen. Nose portion 18 is preferably of circular shape at a juncture with a central portion of head 12 where the central portion has been designated 20 in the drawings.

Figure 4:
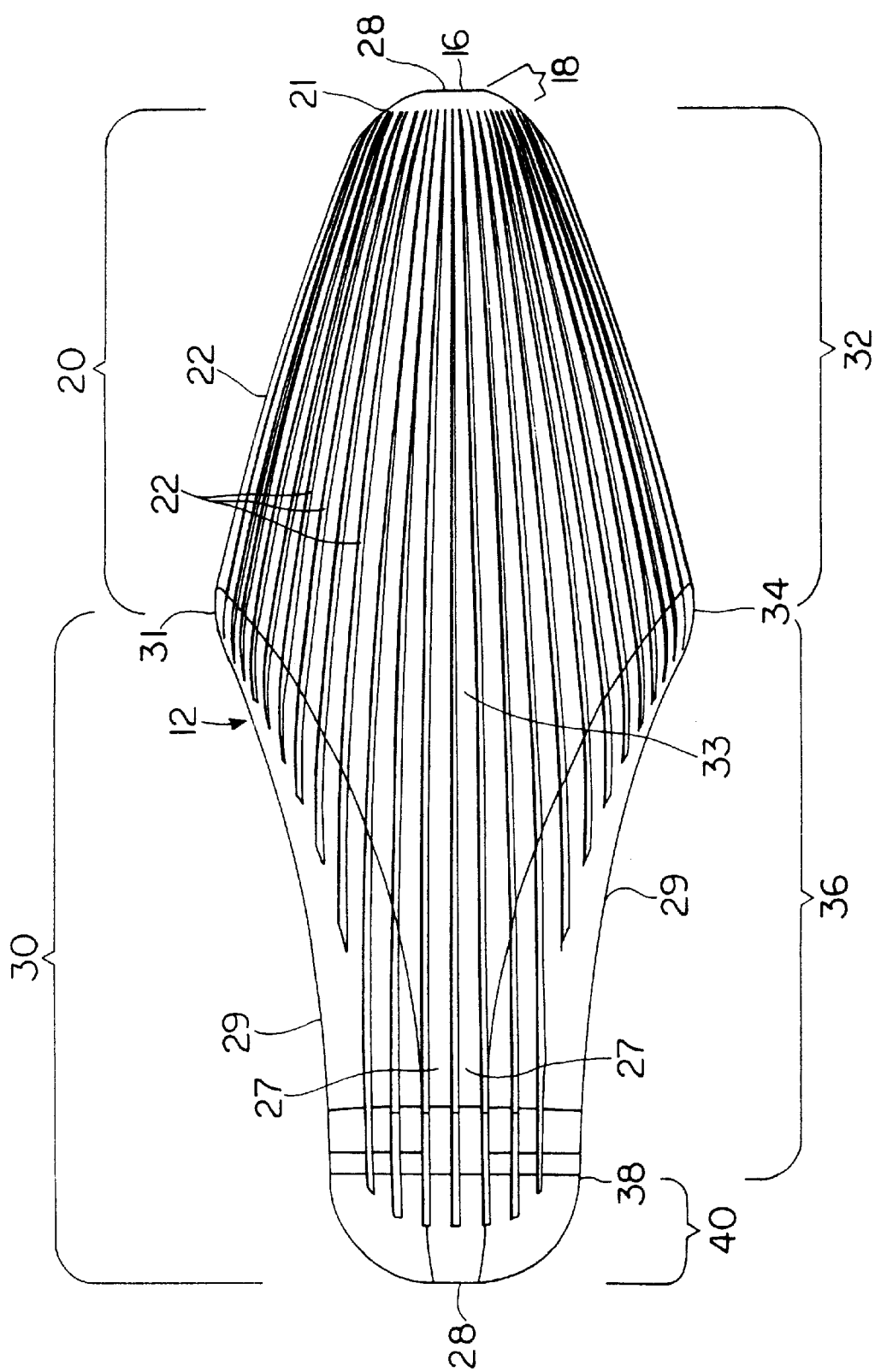
FIG. 4 is a side elevation view of the right side of an atherectomy device in accordance with the invention as illustrated in FIGS. 1, 2 and 3 where the front of the device is to the right in FIG. 4; the left side of the device is a mirror image of FIG. 4.

Central portion 20 commences at the terminus of nose portion 18 which is coincident with the initial portion of longitudinally extending grooves 22 illustrated in FIG. 4. Juncture of nose 18 in central portion 20 is denoted 21 in FIG. 4. Similarly, juncture of central portion 20 and tail portion 30 is denoted 31 in FIG. 4. The position of juncture of central portion 20 and tail portion 30 designated 31 in FIG. 4 is defined by terminus of the shortest one of longitudinally extending cutting grooves 22 where the shortest groove is designated $22_s$ in FIG. 5.

Tail portion 30 is separated from nose portion 18 by central portion 20 with tail portion 30 defining a rear extremity of rotatable head 12 as rotatable head 12 passes through the lumen. Tail portion 30 is preferably of rectangular transverse cross section and tapers from a first generally rectangular transverse cross section at juncture with central portion 20 to a second generally rectangular transverse cross section having a larger maximum diameter at a rear extremity of rotatable head 12.

Central portion 20 preferably tapers from and connects to nose portion 18 with central portion 20 first tapering to a larger cross sectional area at central transition portion 34 and then being of substantially constant circumference and with maximum diameter increased as central portion 20 tapers to join tail portion 30 at juncture position 31 marked in FIG. 4.

As further illustrated in the drawings, head 12 is equipped with very, very small grooves which taper from a fine point at their start, proximate to nose portion 18. This facilitates removal of only very fine particles of plaque or thrombus, thereby avoiding the removal of large chunks of plaque which might embolize and cause difficulty to the patient. Rotatable head 12 is rotatably driven by a source of power provided thereto via a catheter designated generally 13 in the drawings.

Figure 11:
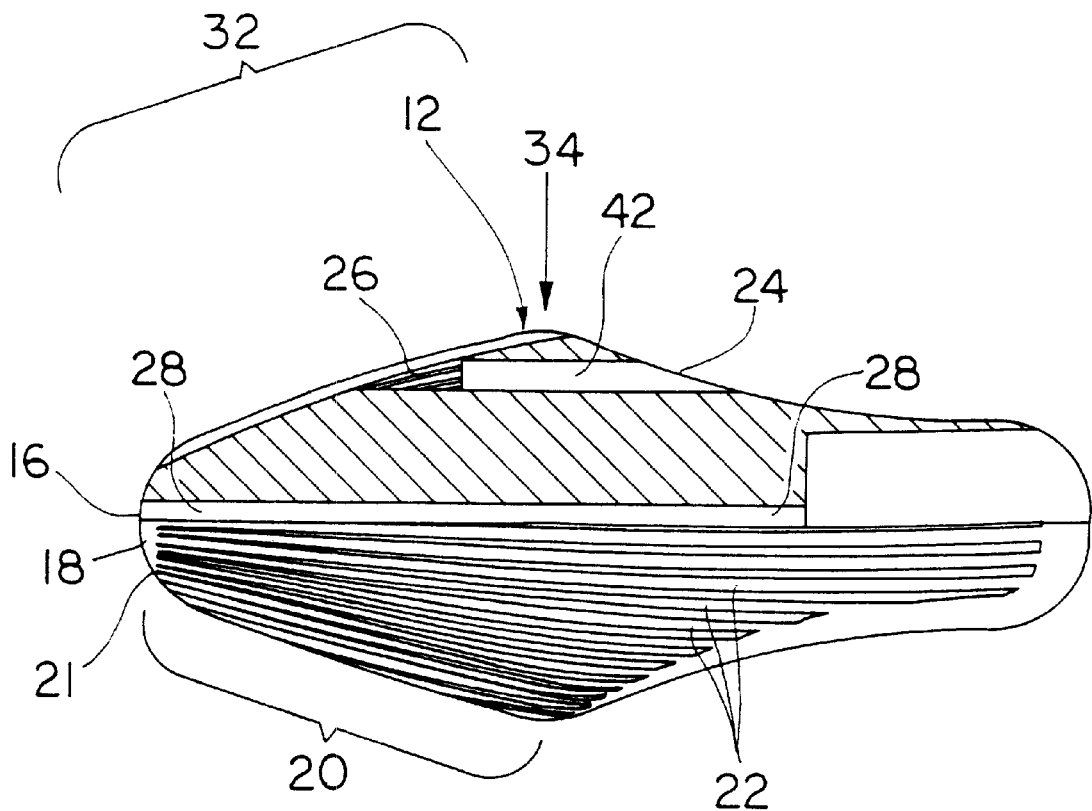
FIG. 11 is a partially sectioned side view of an atherectomy device in accordance with the invention as illustrated in FIGS. 1 through 10 where the sectioned portion illustrated in FIG. 11 is taken along the portion of sectional line 11—11 in FIG. 10, which is drawn vertically.
Figure 12:
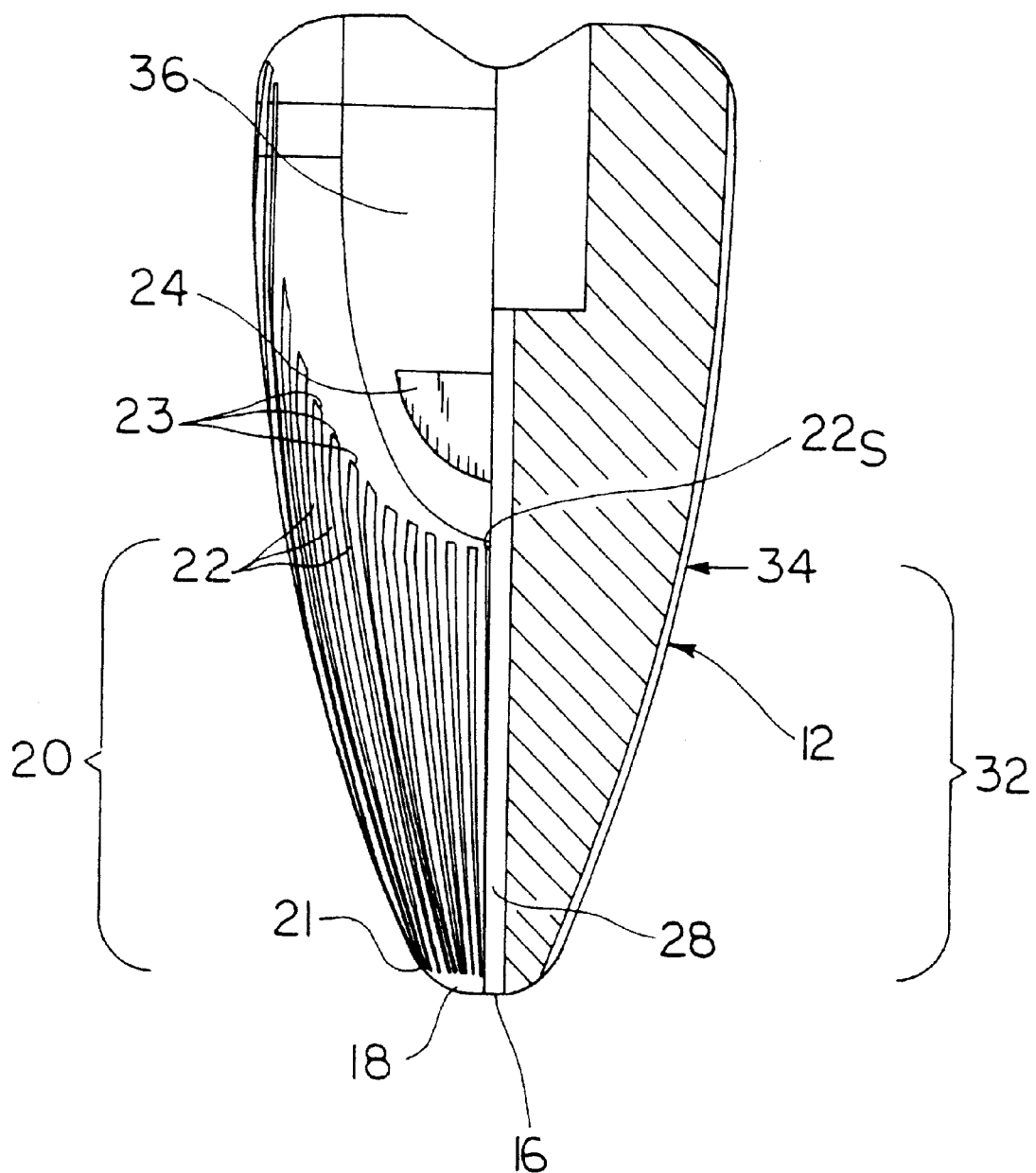
FIG. 12 is a partially sectioned top view of an athrectomy device in accordance with the invention as illustrated in FIGS. 1 through 11 with the sectioned portion taken along the horizontal portion of section line 11—11 in FIG. 10.

Referring to FIGS. 11 and 12 of the drawings, rotatable head 12 preferably has at least two separate and distinct longitudinal passageways therethrough; a first centrally located longitudinally extending passageway 28 is provided for guide wire 14 and is coincident with the longitudinal axis of head 12. A second passageway 42 is formed in head 12 and commences at one end with inlet slits 26 that allow passage of broken-up plaque and other residue material therethrough and an outlet aperture 24 for the efflux of the broken-up plaque, thrombus and other residue material. Passageway 42 functions to remove plaque and other residue material as rotatable head 12 progresses through the lumen. As is apparent from the drawings, two passageways 42 are preferably provided within head 12; the outlets from the two second passageways 42 are visible in FIG. 9.

As illustrated in FIGS. 1, 2, 3, 6, 11, and 12, the front end of rotatable head 12 includes an aperture 16 coincident with central longitudinally extending passageway 28 for facilitation of passage of guide wire 14 therethrough. The portion of head 12 defined by the area from the edge of front aperture 16 to the commencement of longitudinally extending cutting grooves 22 defines a nose portion 18.

Coincident with and adjoining nose portion 18 is a bulbously outwardly curved part 32 of central portion 20, which is defined by extension from commencement of longitudinally extending cutting grooves 22 to a central transition portion 34 defined by the juncture between bulbously outwardly curved portion 32 and an inwardly curved portion 36.

A central transition point 34 defines the beginning of an inwardly curved portion 36 of rotatable head 12, extending from central transition portion 34 to a tail transition portion 38.

A tail transition portion 38 defines the transition from the inwardly curved portion 36 to the curved tail portion 40.

Curved tail portion 40 defineds the terminus of end portion 30. Enlarged end portion 30 accommodates a device, preferably a catheter, to rotate the rotating head 12 and allows for passage of guide wire 14 therethrough.

The surface of the exterior of the rotatable head 12 comprises a plurality of longitudinally extending cutting grooves 22. The longitudinally extending cutting grooves 22 may extend from the edge of nose 18 to the tail transition portion 38 of the rotating head 12.

Figure 5:
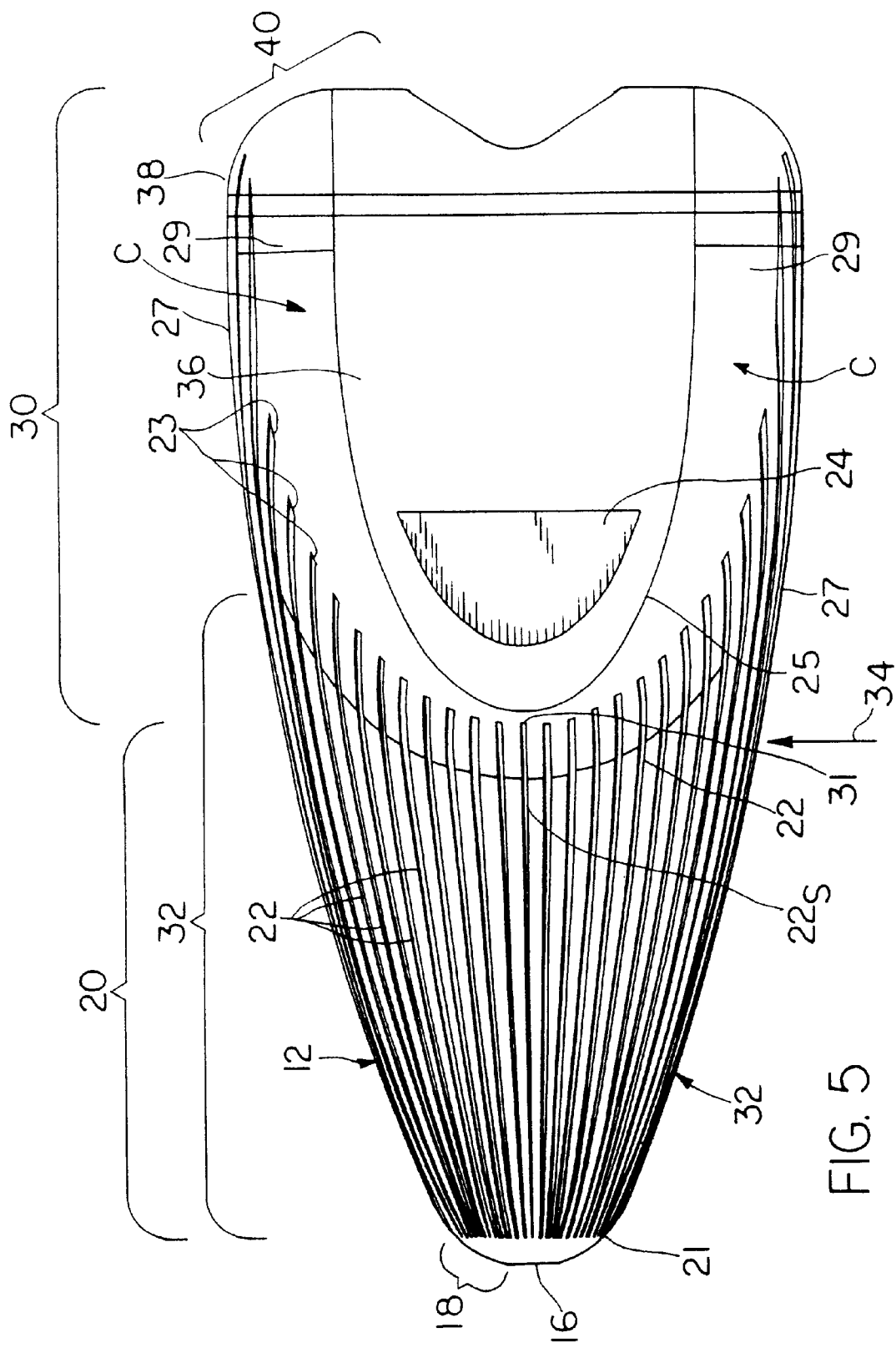
FIG. 5 is a top view of an atherectomy device in accordance with the invention as illustrated in FIGS. 1, 2, 3 and 4 where the front of the atherectomy device is to the left in FIG. 5; the bottom of the device is a mirror image of FIG. 5.

As illustrated in FIGS. 4 and 5, the taper of the inwardly curved portion 36 is preferably not constant over the entire exterior surface of rotatable head 12. FIG. 4 shows the portion of rotatable head 12 ahead of inwardly curved portion 36 including longitudinally extending cutting grooves 22 extending from the edge of nose 18 towards central transition portion 34 and varying in length consistent with the degree of taper from bulbously outwardly curved portion 32 to inwardly curved portion 36. Specifically, the taper is visible on comparison of FIGS. 4 and 5 wherein the inwardly curved portion 36 defines two mirror image surfaces of rotating head 12 and bulbously outwardly curved portion 33 extending the length of rotatable head 12. As is apparent from FIGS. 4 and 5, particularly FIG. 5, head 12 from nose portion 18 through central portion 20, growing in cross sectional size from nose portion 18 to central transition portion 34. Cutting grooves 22 are preferably of substantially constant width and, accordingly, space between adjacent grooves increases proceeding from nose portion 16 along the axial length of head 12.

Ends of longitudinally extending cutting grooves 22 which are remote from nose 18 are designated generally 23 in FIGS. 4 and 5. Inboard of ends 23 is a line of surface demarcation 25, shown in FIGS. 5, 6 and 7, which divides the top and the bottom surfaces of head 12 into different regions. In a region outboard of line 25, as indicated by arrow C in FIG. 5, the exterior surface of head 12 transitions from a vertical surface at the position indicated by numeral 27 in FIGS. 4 and 5 to horizontal as indicated by numeral 29 in FIGS. 4 and 5.

Figure 6:
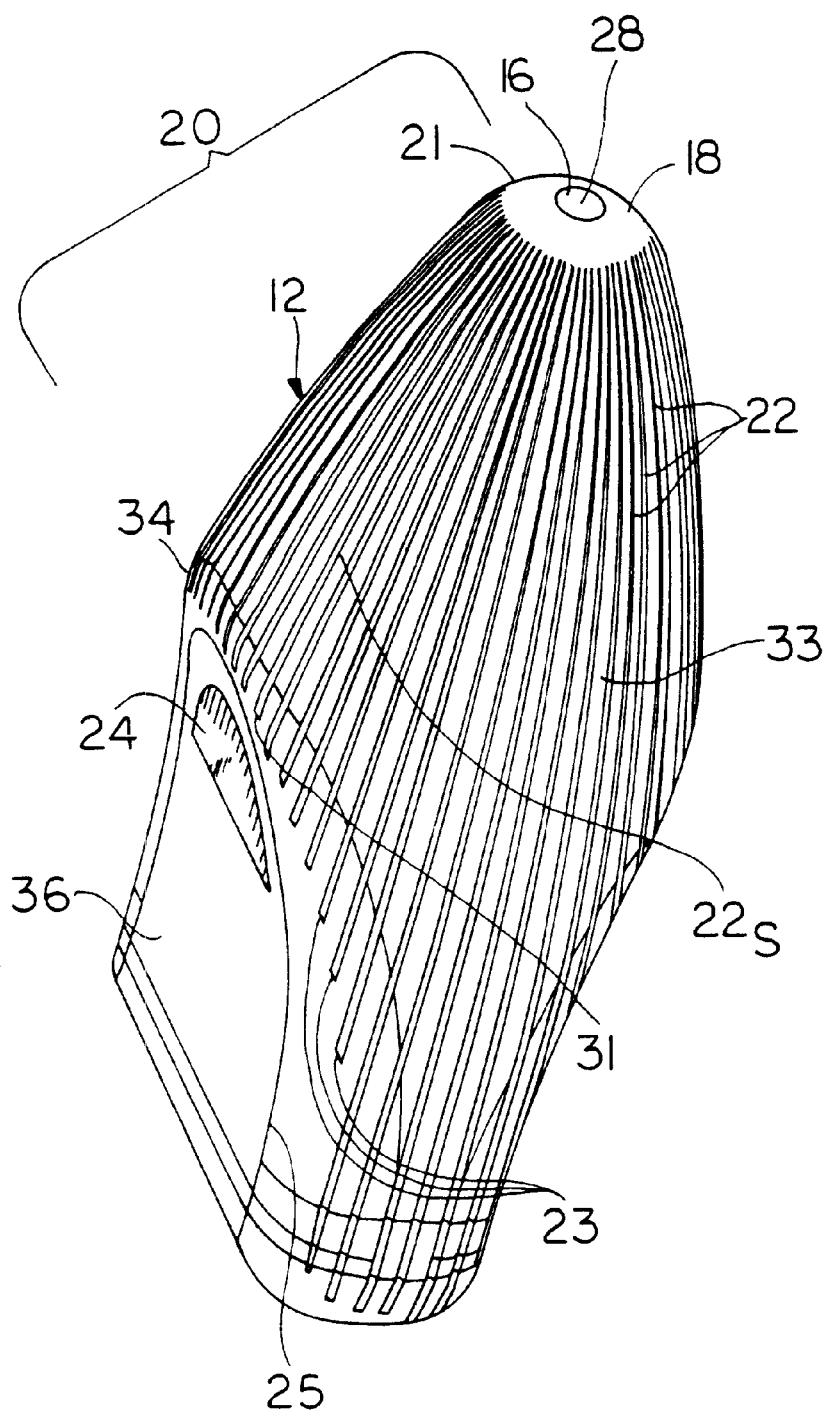
FIG. 6 is an isometric view of an atherectomy device in accordance with the invention illustrated in FIGS. 1, 2, 3, 4 and 5, showing the front, the top and the right sides of the device, with the front of the device pointing generally upwardly.
Figure 7:
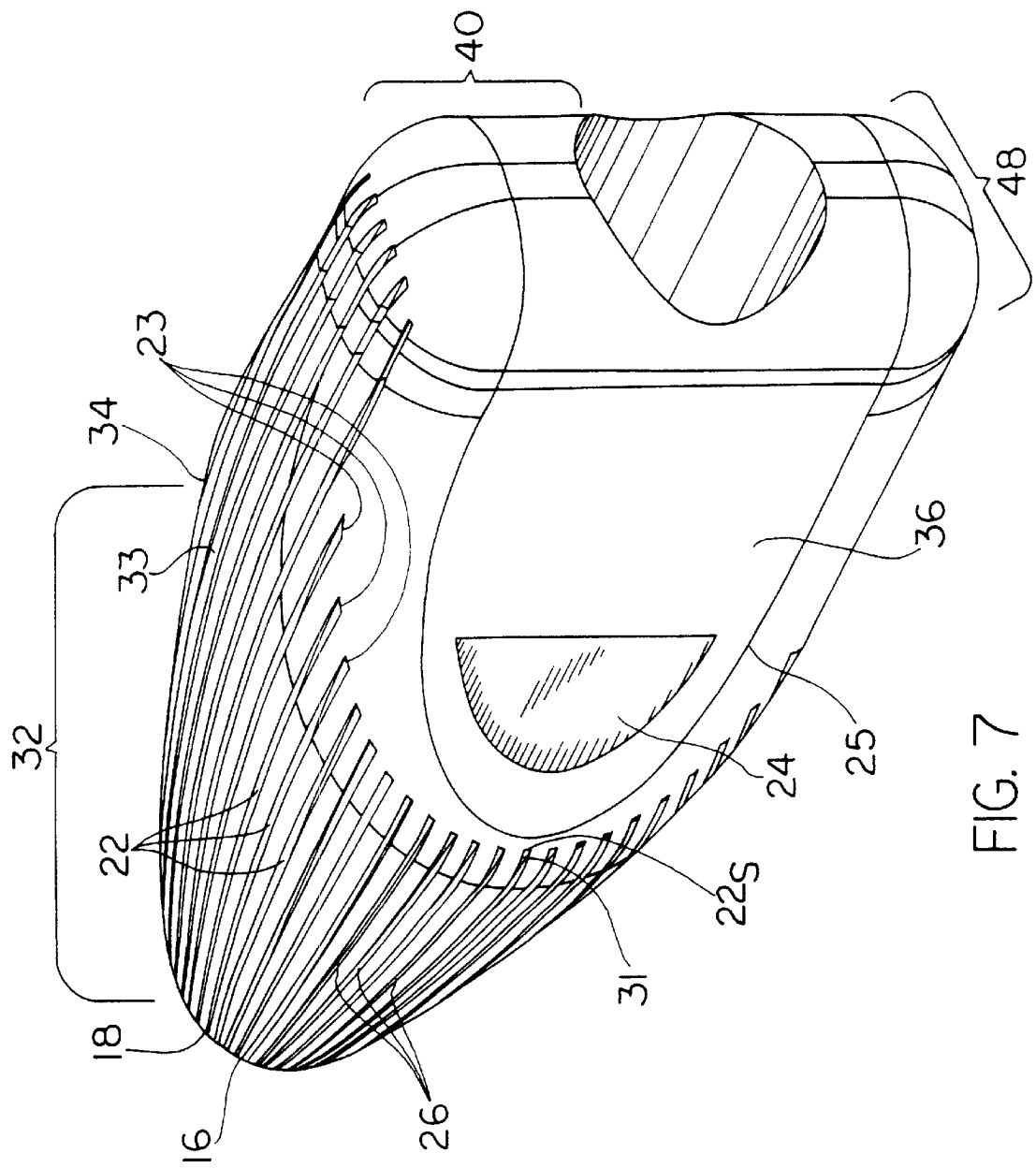
FIG. 7 is an isometric view of an atherectomy device in accordance with the invention illustrated in FIGS. 1, 2, 3, 4, 5 and 6, showing the rear, the top and the right side of the device, with the front of the device pointing generally away from the viewer.

Inboard of line of surface demarcation 25 the outwardly facing surface portion of head 12, denoted 36 in FIG. 5, is concave as illustrated in FIGS. 6 and 7 as well as in FIG. 4.

FIG. 5 illustrates the varying length of the longitudinally extending cutting grooves 22 and the pattern thereof. An end enlarged portion 30 depicted in FIG. 5 allows for passage of a guide wire 14 and accommodates a device, preferably a catheter, to rotate rotating head 12. An outlet aperture 24 for the efflux of plaque and residue material from grooves 22 is within inwardly curved portion 36 of rotatable head 12.

FIG. 6 illustrates the bulbously outwardly curved surface portion 33 and longitudinal cutting grooves 22 that extend the length of rotating head 12. The bulbously outwardly curved surface portion 33 contains all of grooves 22 and is contiguous with inwardly curved surface portion 36 of rotatable head 12. Within inwardly curved portion 36 is an outlet aperture 24 from second passageway 42 that allows for the efflux of plaque and residue material. The general cone shape of the front end and transition to the inwardly curved surface portion 36 of rotating head 12 is shown in FIG. 6.

A view from the tail end of the rotating head 12 towards the front end of the rotating head 12 is depicted in FIG. 7. FIG. 7 illustrates the narrow width of the tail end 48 and the inverse tapering of inwardly curved portion 36 towards central transition portion 34 and from there along bulbously outwardly curved portion 32 towards nose 18 of rotating head 12. The gradual tapering from inwardly curved portion 36 to bulbously outwardly curved portion 33 that extends the length of the rotating head 12 is also depicted.

Figure 8:
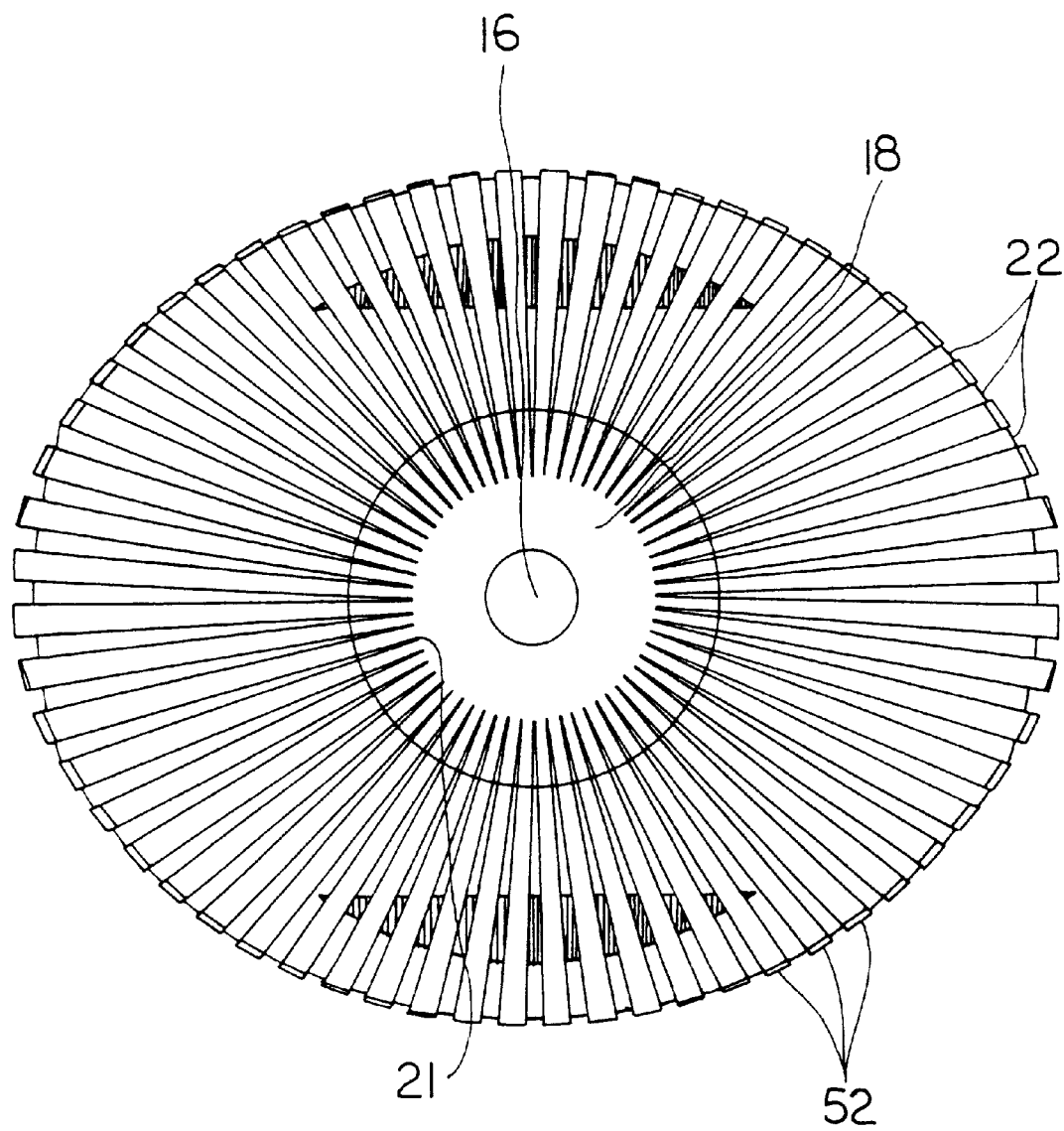
FIG. 8 is a front view of an atherectomy device in accordance with the invention as illustrated in FIGS. 1 through 7.

A round front aperture 16 for a guide wire 14 defines the axis rotating head 12. FIG. 8 depicts a view looking into the front aperture 16 of the rotating head 12. The nose 18 of rotating head 12 is the area extending from commencement of the longitudinally extending cutting grooves 22 to the exterior circumference of front aperture 16. The longitudinally extending cutting grooves 22 comprise a plurality of points defining the edge of the nose 18. Longitudinally extending cutting grooves 22 are separated by a series of ridges 52.

Figure 9:
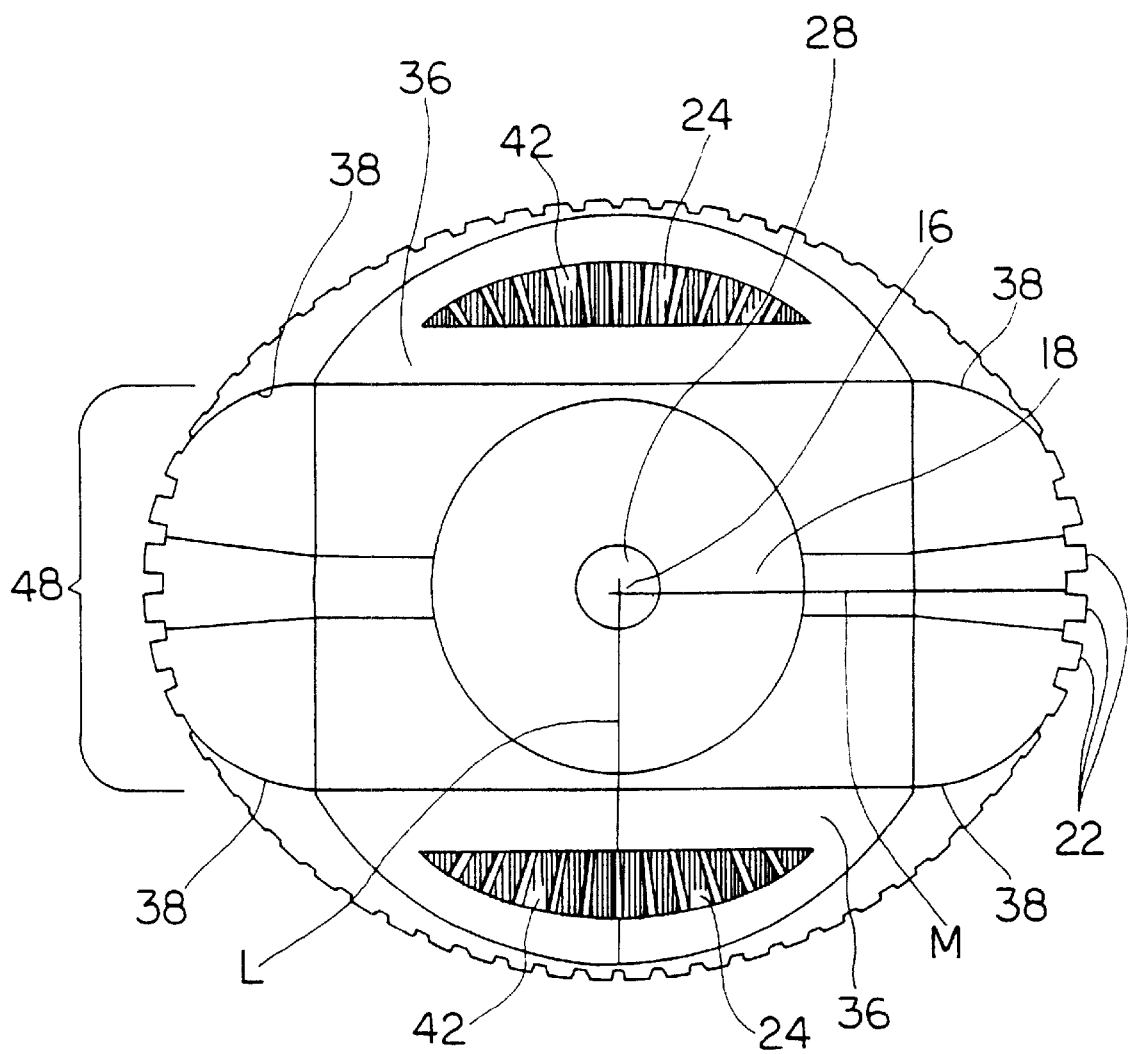
FIG. 9 is a rear view of an atherectomy device in accordance with the invention as illustrated in FIGS. 1 through 8.

A view from the tail of rotating head 12 towards nose 18 is depicted in FIG. 9. Circumference of the rotating head 12 is constant from central transition point 34 substantially to the remote extremity of tail portion 30 where diameter measures at the inwardly curved portion 36 M is not the same as diameter L of the bulbously outwardly curved portion 38. The narrow width of the tail end 48 compensates for the bulbously outwardly curved portion 32, allowing for the same circumference. Tail portion 30 accommodates a device for rotating the rotating head 12 as well as the central longitudinally extending passageway 28 for the guide wire 14. FIG. 9 also illustrates the view into the outlet aperture 24 for the efflux of plaque and residue material.

Figure 10:
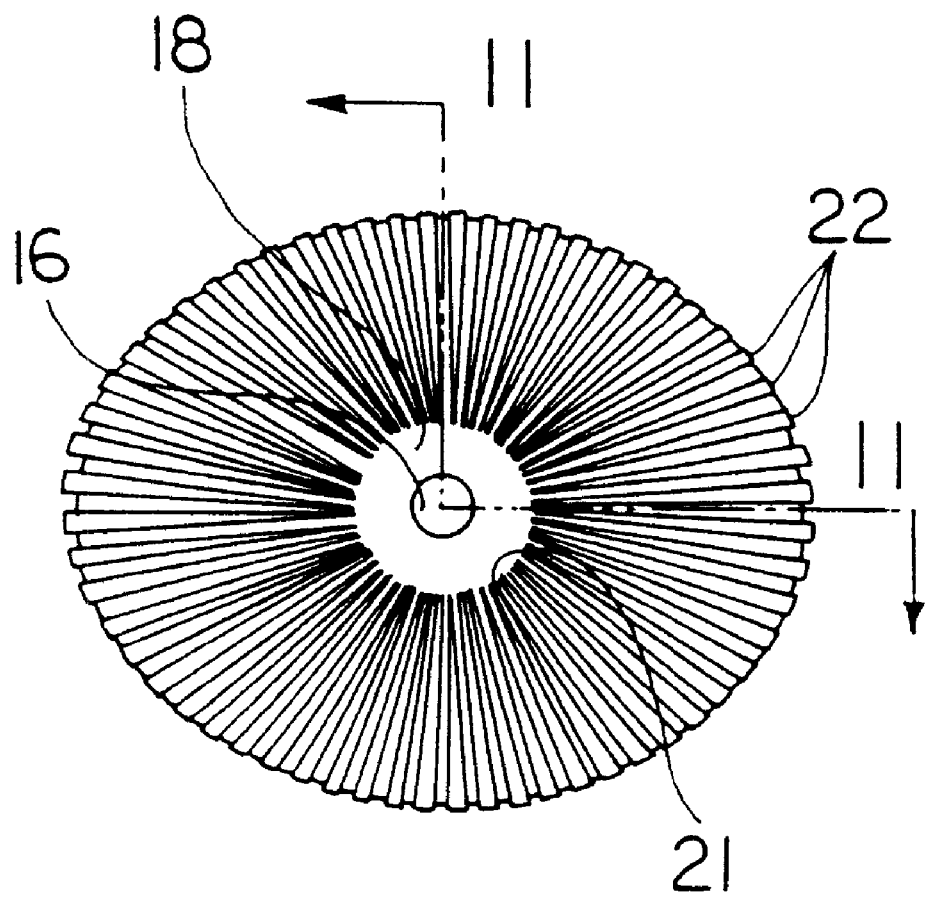
FIG. 10 is a front view similar to FIG. 8 of an atherectomy device in accordance with the invention as illustrated in FIGS. 1 through 9, with section lines 11—11 appearing thereon.

Shorter longitudinally extending cutting grooves 22 on bulbously outwardly curved portion 32 of rotating head 12 accommodate inlet slits 26 for passage of plaque and residue material in the channels between the ridges of the longitudinally extending cutting grooves 22, into second passageways 42. The view into the nose 18 of the rotating head 12 is depicted in FIG. 10.

FIG. 11 depicts a cutaway of a portion of rotating head 12. The view depicts the bulbously outwardly curved portion 32 and the longitudinally extending cutting grooves 22. The figure shows the internal portion of the rotating head 12. Depicted is the central longitudinally extending passageway 28 for a guide wire 14 contiguous with the tail portion 30 that accommodates a device for rotating the rotating head 12. The second passageway 42 is depicted connecting inlet slits 26 with outlet aperture 24 that allow for the efflux of plaque and residue material through rotating head 12.

In FIG. 12 central longitudinally extending passageway 28 for a guide wire 14 is coincident with the tail portion 30 for accommodation of a device to rotate head 12. A bulbously outwardly curved portion 32 transitioning at a central transition portion 34 to the inwardly curved portion 36 is depicted showing an outlet aperture 24 for the efflux of plaque and residue material.

Figure 24:
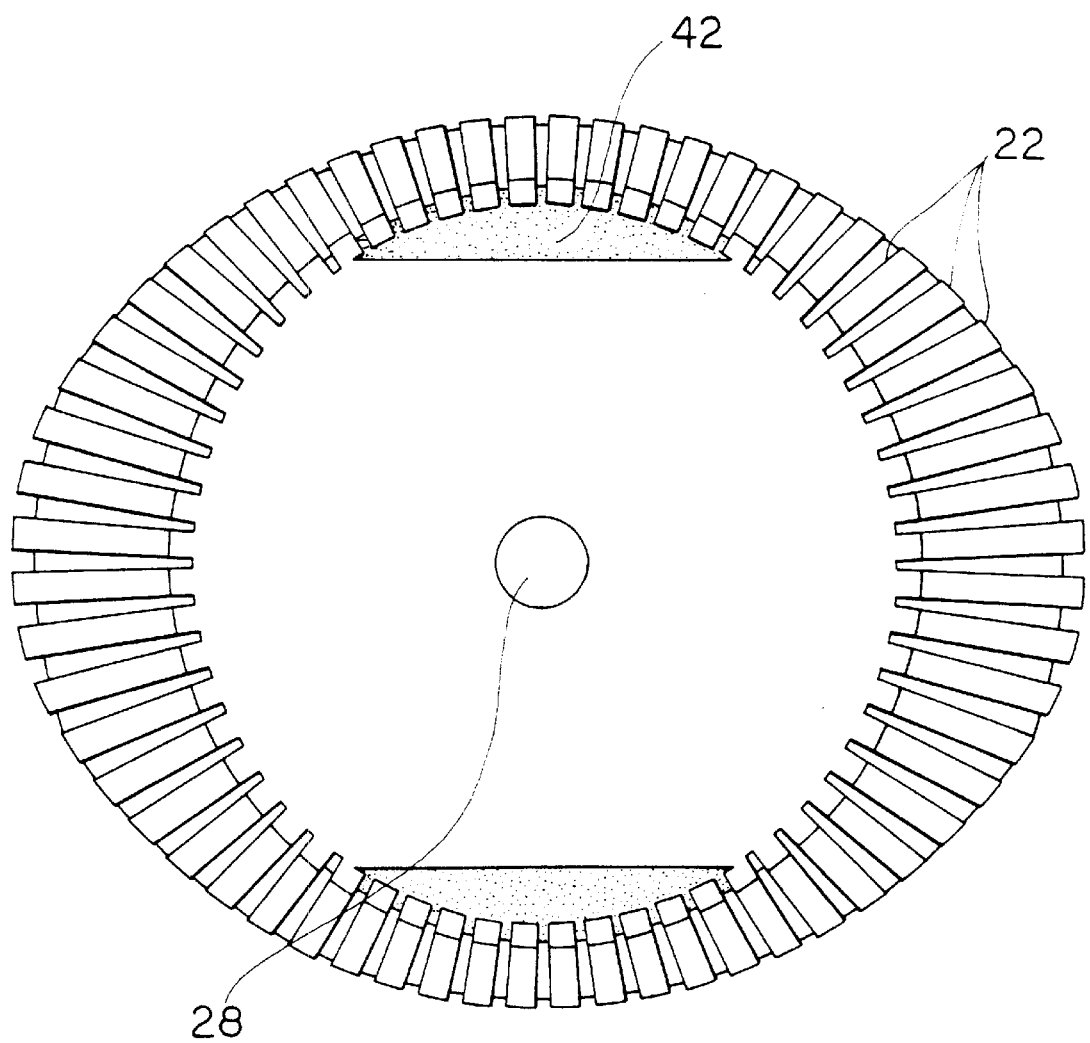
FIG. 24 is a front view looking towards the rear of the truncated athrectomy device illustrated in FIG. 23.

A cross-sectional view into the front end of a rotatable head 12 with the front end removed is shown in FIG. 24. A central longitudinally extending passageway 28 that facilitates passage of a guide wire 14 therethrough defines the center of the rotatable head 12. In FIG. 24 a second passageway 42 on each side of central longitudinally extending passageway 16 allows passage of plaque and thrombolytic material therethrough. Ridges and depressions defined by a plurality of longitudinally extending cutting grooves 22 are shown.

Figure 23:
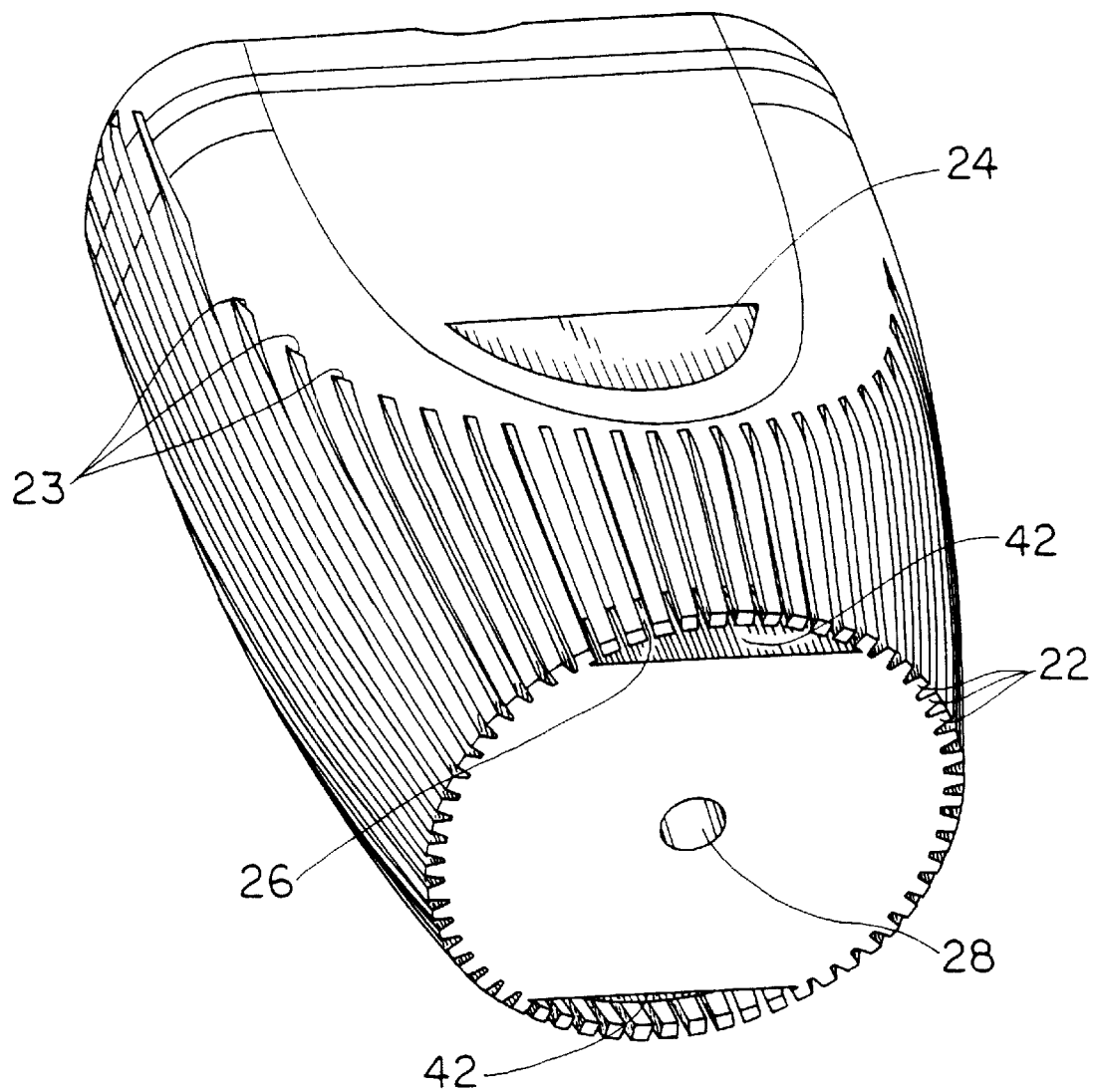
FIG. 23 is an isometric view of an athrectomy device in accordance with the invention as illustrated generally in FIG. 22, cut along sectional line 23—23 in FIG. 22, with the portion of the athrectomy device in front of that line having been removed.

Second passageway 42 is also shown in FIG. 23, a cross-sectional view into the front portion of the rotatable head 12.

Figure 22:
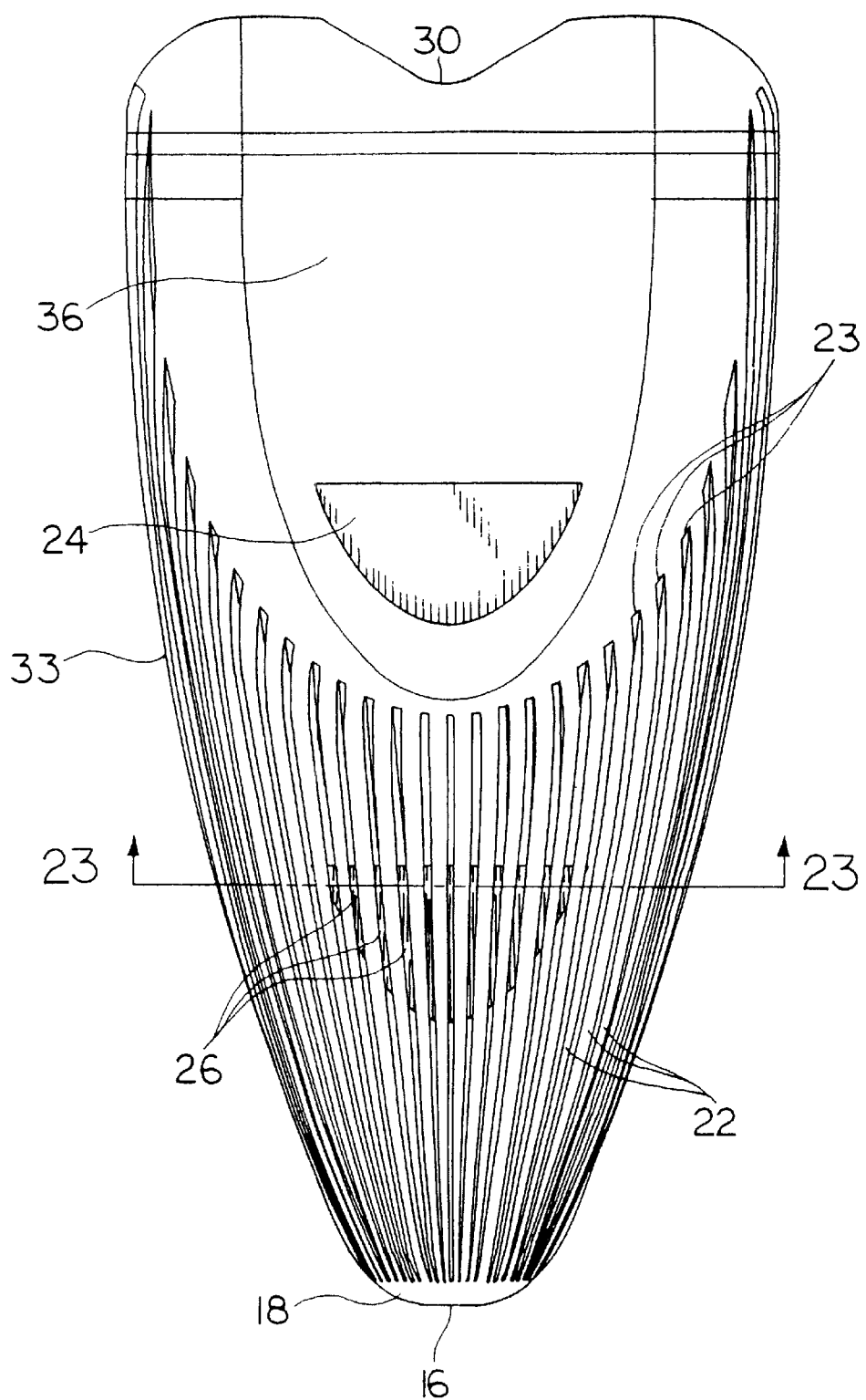
FIG. 22 is a top view of an athrectomy device in accordance with the invention as illustrated generally in FIGS. 1 through 9 with a shaded area depicting the area of inlet to a debris channel passing through the athrectomy device.

Inlet slits 26 allow the influx and removal of plaque and thrombolytic material via second passageway 42. Slits 26 define openings into second passageway 42 between the ridges separating the longitudinally extending cutting grooves. As shown in FIG. 22 the inlet slits 26 allow influx of material through the second passageway 42 and outlet aperture 24.

Figure 13:
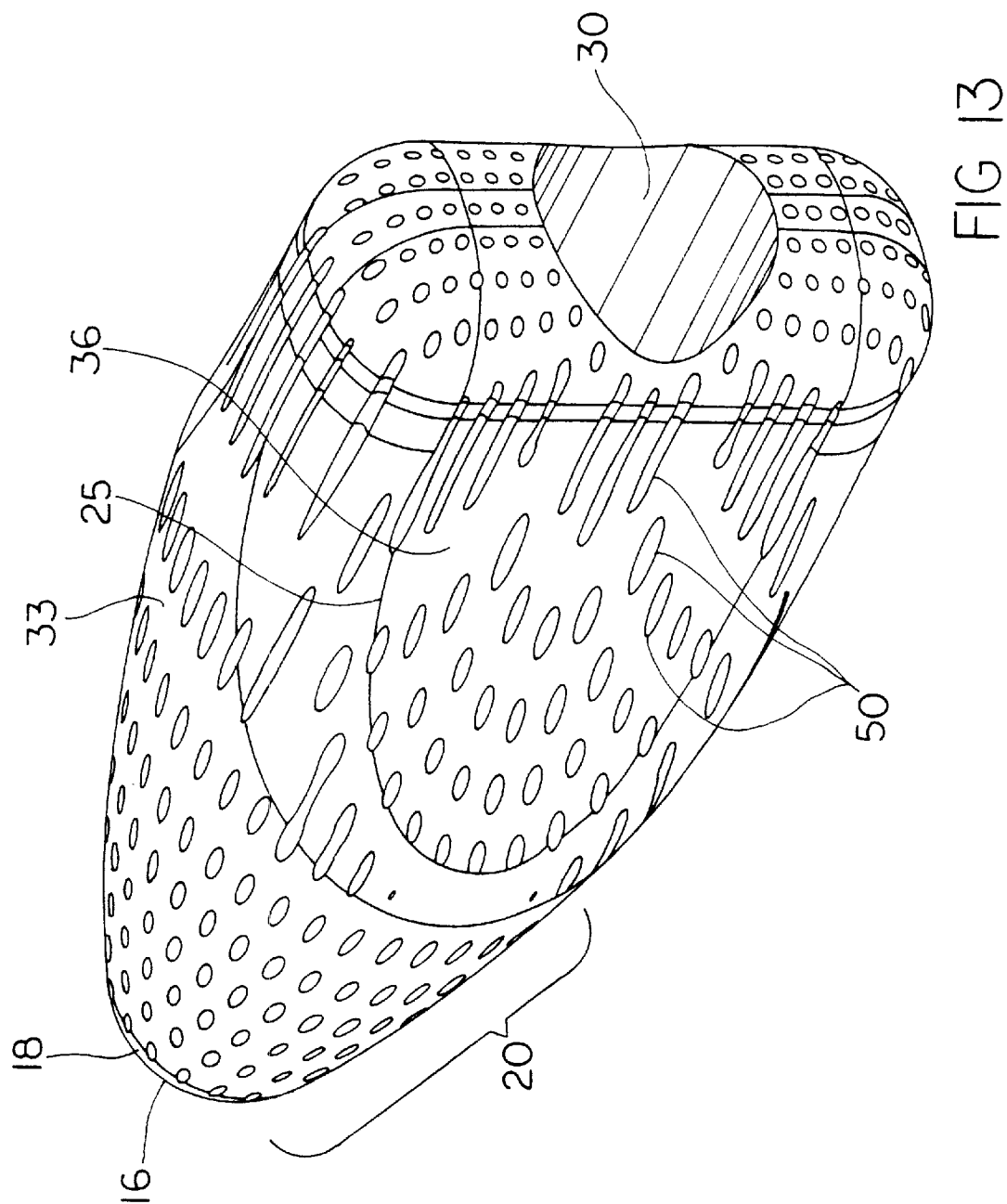
FIG. 13 is an isometric view showing the rear, top and right side of a second embodiment of an athrectomy device in accordance with the invention, with the front of the device pointing generally away from the viewer; the orientation of the athrectomy device in FIG. 13 is similar to that of FIG. 7.

An alternative embodiment of the atherectomy device 10 is defined by the incorporation of a plurality of cutting indentions or cutting divots 50 in lieu of longitudinally extending cutting grooves 22, as shown in FIG. 13, where the divots 50 vary from circular to oblong. The divots 50 function to remove plaque and thrombolytic material from the interior of veins and arteries in the human body, in the same fashion as the longitudinally extending cutting grooves 22, as head 12 rotates.

A divot 50 is one of three options for the embodiment shown in FIG. 14. The embodiment defined by divot 50 is labeled 14-3.

Alternatively these may be round or oblong holes in the rotating head 12, designated 14-1, and passing entirely longitudinally therethrough, a cup shaped cutting surface in the rotating head designated 14-2 or a divot like cutting surface indention designated 14-3.

Figure 15:
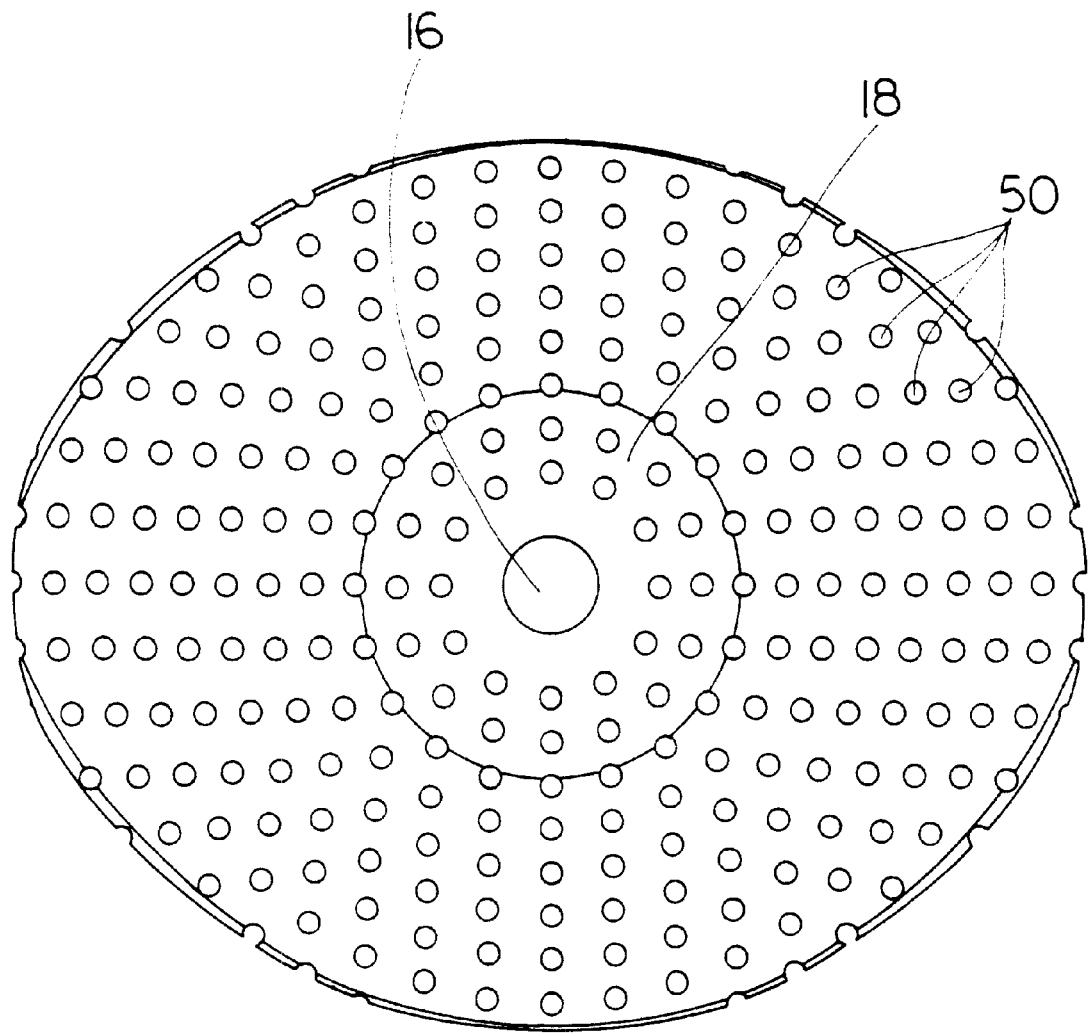
FIG. 15 is a front view of the embodiment of the athrectomy device illustrated in FIGS. 13 and 14-1.

As shown in FIG. 15 looking into the nose 18 of the rotatable head 12 a front aperture defines the center of the front end of the rotatable head 12 wherein the front end is defined by a plurality of divots 50.

Figure 16:
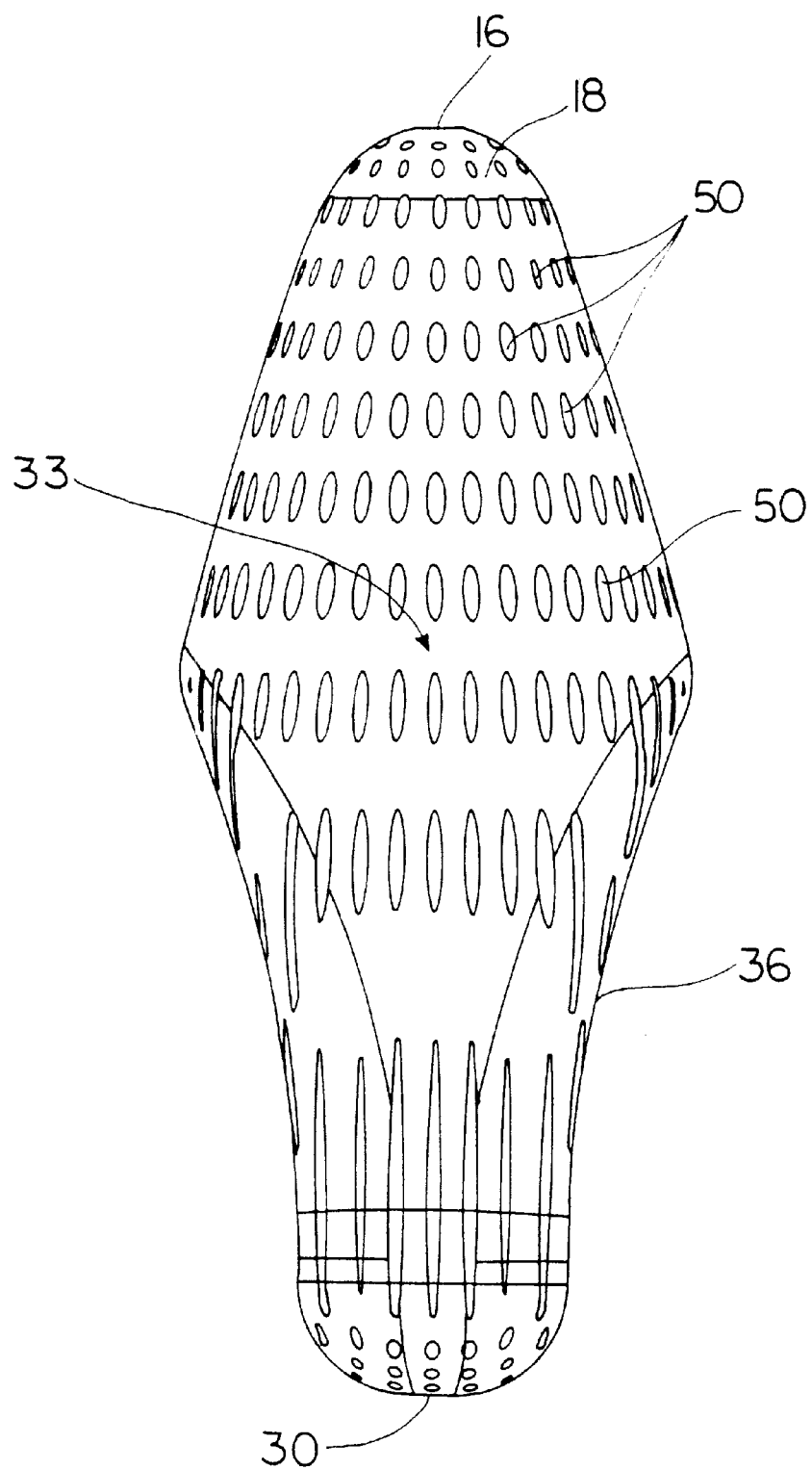
FIG. 16 is a side elevation of the athrectomy device illustrated in FIGS. 13 through 15.

The divots 50 extend from the front end of the rotatable head 12 to the tail end of the rotatable head 12, covering the exterior of the rotatable head 12 with divots 50 of varying sizes shown in FIG. 16.

Figure 17:
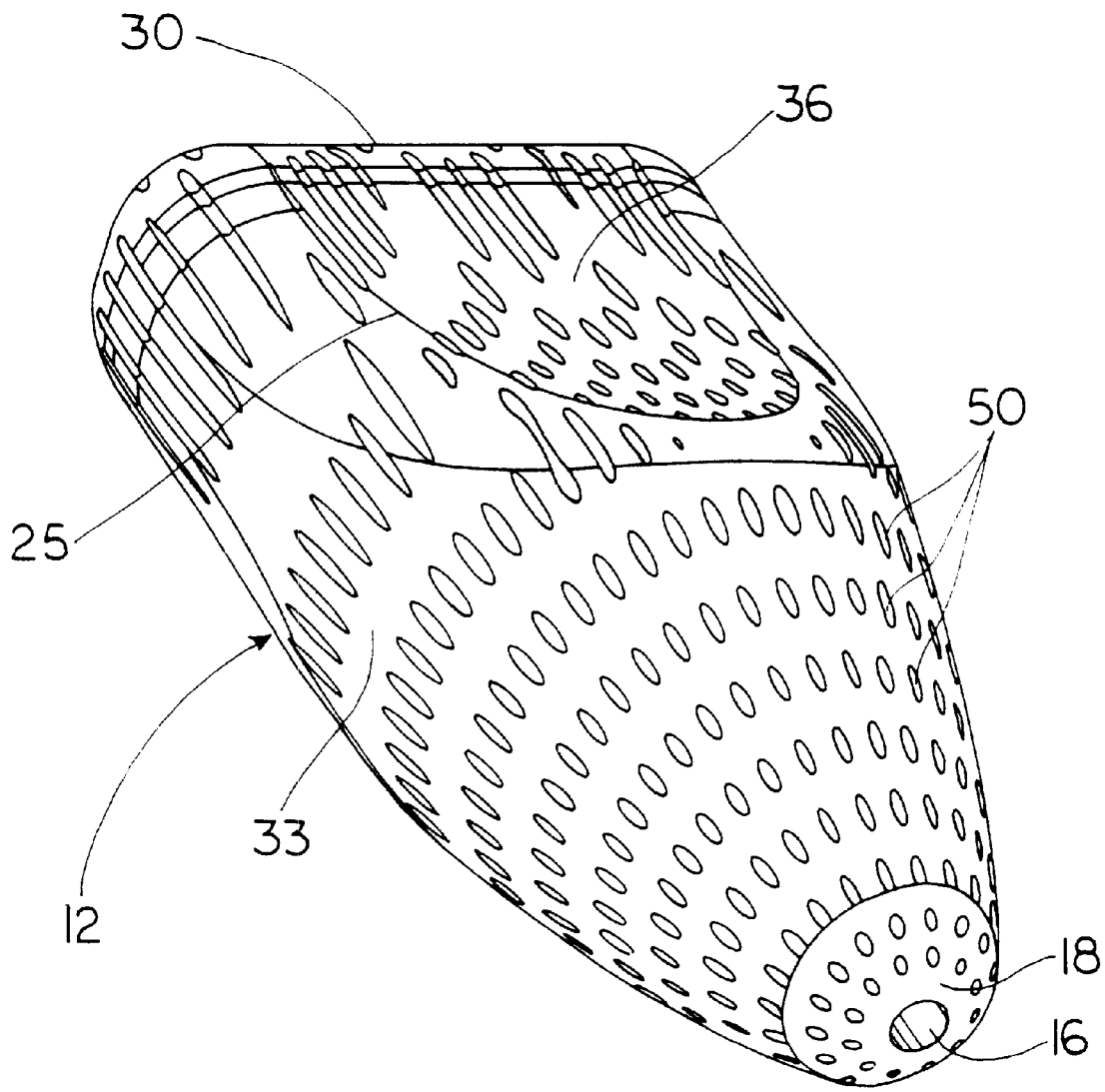
FIG. 17 is an isometric view of the front, top and right side of the athrectomy device illustrated in FIGS. 13 through 16.

A view from the front end of rotatable head 12 towards the tail end of rotatable head 12 depicts divots 50 of varying dimensions consistently covering the exterior of the rotatable head 12 along the bulbously outwardly extending portion 32 and the inwardly curved portion 36. FIG. 17 also depicts the divots 50 within the nose portion 18.

Figure 18:
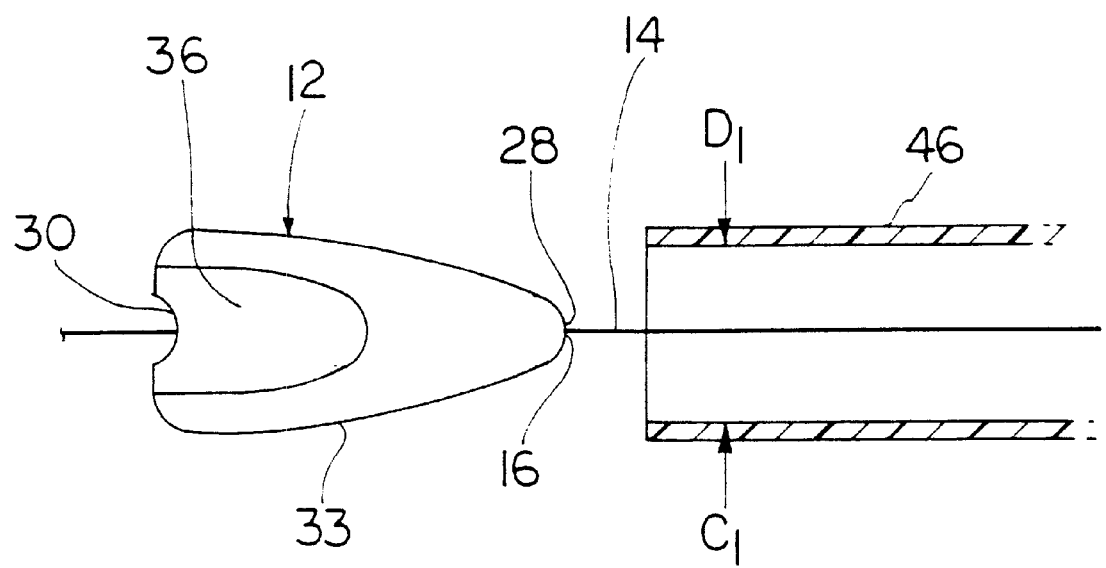
FIG. 18 is a schematic view depicting an athrectomy device in accordance with the invention being guided by a wire into a sheath preparatory to entry into the lumen of a patient.

As shown in FIG. 18 the rotatable head 12 facilitated by guide wire 14 extending beyond the front end of the rotatable head 12 through a central passageway 28 enters a sheath 46 having diameter D1 and circumference C1.

Figure 19:
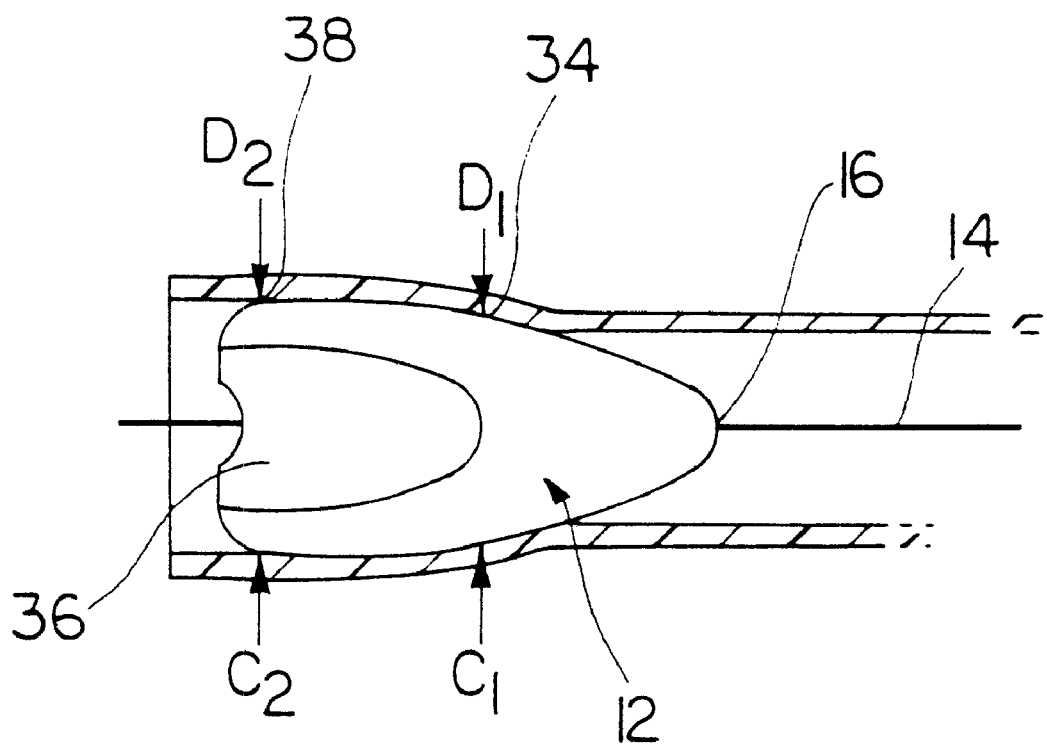
FIG. 19 is a schematic depiction similar to FIG. 18 showing the athrectomy device within the sheath.

FIG. 19 shows the distortion of the sheath resulting from insertion of rotatable head 12 having circumference C1 and diameter D1 at central transition portion 34 and circumference C2 at tail transition portion 38 which equal to C1. However "diameter" D2 at tail transition portion 38 exceeds D1. Of course "diameter" of head 12 measured at the location designation by C2 but in a direction perpendicular to the plane of the paper is much less than D2; this is apparent from FIG. 9. Distortion of the sheath facilitates passage of rotatable head 12 therethrough.

Figure 20:
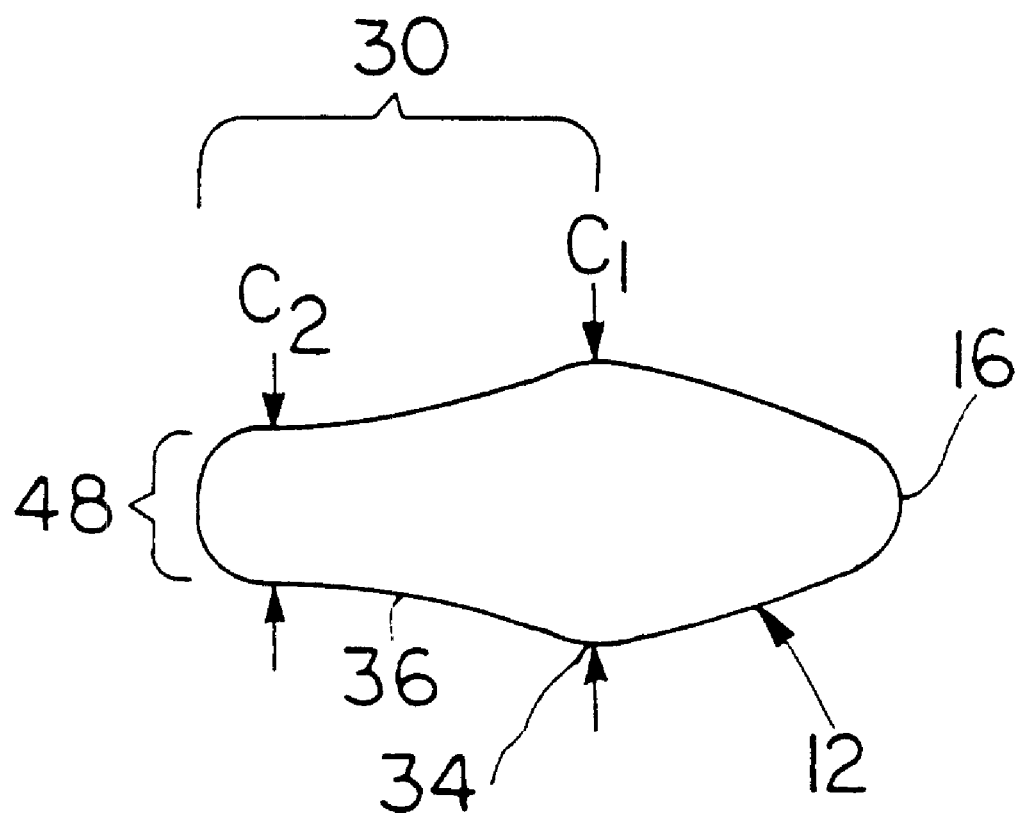
FIG. 20 is a schematic representation of an athrectomy device in accordance with the invention rotated ninety degrees (90°) relative to FIGS. 18 and 19, illustrating certain geometric features.

Rotatable head 12 shown in FIG. 19 has been rotated 90 degrees in FIG. 20 to depict that narrow tail portion 48 has the same circumference C2 as circumference C1 at the central transition portion 34; the "pinched" aspect of tail portion 30 which is not discernable in FIG. 18 and 19 is shown in FIG. 20.

Figure 21:
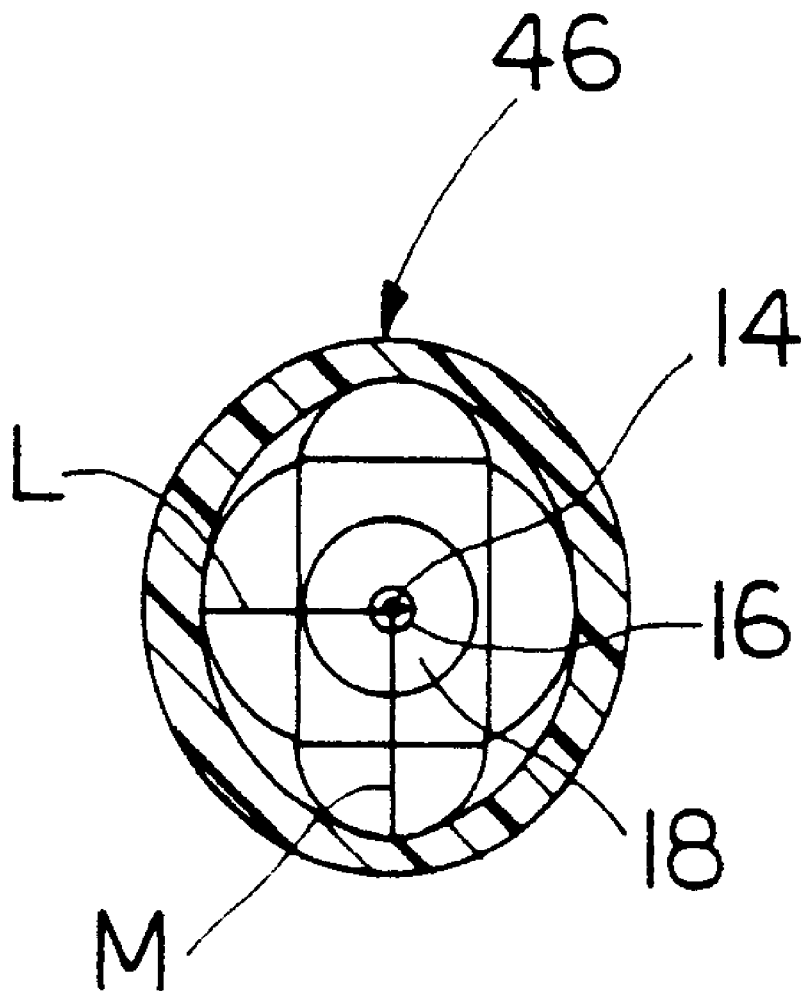
FIG. 21 is a front view of the athrectomy device in accordance with the invention within the sheath as illustrated in FIGS. 18 and 19.

A view within the sheath towards tail portion 30 of rotatable head 12 towards nose portion 18 is shown in FIG. 21. The constant circumference C2 narrow tail portion 48 and circumference C1 at central transition portion 34 is apparent and allows the rotatable head to pass through the sheath 46.

An expandable sheath inserted into the artery accommodates the increased size of the rotatable head 12 and facilitates insertion of the rotatable head 12 into the artery, functioning to minimize the access size and trauma to the patient.

Rotatable head 12 has a constant circumference from the central transition portion 34 to the end transition portion 38 while maximum diameter at central transition portion 34 is less than diameter at end transition portion 38. The relationship between outwardly extending surface portion 33 and inwardly curved surface portion 36 allow for increased diameter D2 while circumference C2 remains constant; as diameter increases along the outwardly extending portion 33, inwardly curved surface portion 36 reduces width of head 12 proportionately.

The narrow width of tail end 48 of rotatable head 12 created by the inwardly curved surface portion 36 of the tail 30 of rotatable head 12 allows an increased diameter D2 while retaining constant circumference C2. Smaller diameter D1 at transition portion 34 facilitates entry into the sheath and hence into a lumen wherein the rotatable head 12 cleans out at a diameter of D2. In operation, the constant circumference maintains consistent distortion of the lumen and minimal discomfort to the patient.

What is claimed is:

1. An atherectomy device from removing plaque from the interior of a lumen upon travel of the device therethrough, comprising:
   a. a rotatable head having nose, central and tail portions;
      i. said nose portion being bulbously outwardly curved and defining a forward extremity of said head for initial passage within said lumen, of circular shape at juncture with said central portion, with the center of the circular shape coincident with the longitudinal axis of said head;
      ii. said tail portion being separated from said nose portion by said central portion, said tail portion defining a rear extremity of said head as said head portion passes through said lumen, said tail portion being of rectangular transverse cross-section and tapering from a relatively smaller maximum diameter at juncture with said nose portion to a relatively larger maximum diameter at a rear extremity of said rotatable head;
      iii. said central portion transitionally tapering from and connecting said circular nose portion to said rectangular transverse cross-section tail portion, and central portion being of larger transverse cross-sectional area at juncture with said tail portion than at said juncture with said nose portion;
   b. said head having a plurality of longitudinally extending cutting grooves formed therein commencing proximate juncture of said circular nose portion and said central portion and extending rearwardly therefrom.

2. The atherectomy device of claim 1 wherein said head has a central passageway extending the longitudinal length thereof coincidently with the longitudinal axis of said head, adapted for passage therethrough of means for guiding travel of said head through said lumen.

3. The atherectomy device of claim 1 wherein said tail portion tapers in only one dimension of the rectangular shape.

4. The atherectomy device of claim 3 wherein said tail portion tapers non-uniformly.

5. The atherectomy device of claim 1 wherein said central portion tapers uniformly.

6. The atherectomy device of claim 1 wherein at least some of said cutting grooves in said surface extend along the central portion and the rear portion.

7. The atherectomy device of claim 2 wherein said passageway has an enlarged portion at the rear end of said head for securement of means for rotating said head.

8. The atherectomy device of claim 2 wherein there is a second passageway through said head having an aperture end communicating with said cutting grooves and having a second aperture end formed in a rear section surface portion between juncture of said central and rear sections and the rear extremity of said head.

9. The atherectomy device of claim 1 wherein said cutting grooves extend along surfaces of non-tapering sides of said rectangular cross-section of said tail portion.

10. The atherectomy device of claim 1 wherein said grooves transition longitudinally from v-shaped to rectangular.

11. The atherectomy device of claim 10 wherein at least some of said rectangular portions of said grooves are square.

12. The atherectomy device of claim 1 wherein said grooves have depth no greater than 0.005 inches.

13. The atherectomy device of claim 1 wherein said v-shaped and rectangular portions of some of said grooves have the same depth.

14. The atherectomy device of claim 11 wherein said v-shaped portions of said grooves have depth exceeding groove width at the groove mouth.

15. The atherectomy device of claim 1 wherein groove width increases by a factor of 10 with position along groove longitudinal length.

16. The atherectomy device of claim 1 wherein said grooves extend from said circular nose portion along said central portion at least to a region of constant circumference along the axial direction.

17. The atherectomy device of claim 1 wherein adjacent grooves at said nose portion are separated by a distance about ten times the width of the mouth of said grooves thereat.

18. The atherectomy device of claim 1 wherein the bottom of at least one of said v-shaped grooves in said central portion are open and further comprising a passageway extending part-way through said device connecting at one passage end with said open bottom of said v-shaped groove, a remaining end of said passage exiting from said device in said tail portion.

19. An atherectomy device from removing plaque from the interior of a lumen upon travel of the device therethrough, comprising:

a. a rotatable head having nose, central and tail portions;
   i. said nose portion being bulbously outwardly curved and defining a forward head extremity for initial passage within said lumen;
   ii. said tail portion being separated from said nose portion by said central portion, said tail portion defining a rear extremity of said head as said head portion passes through said lumen; said tail portion being of rectangular transverse cross-section and tapering from a smaller maximum diameter section at juncture with said center portion to a larger maximum diameter at a rear extremity of said rotatable head;
   iii. said central portion transitionally tapering from and connecting said circular nose portion to said rectangular transverse cross-section tail portion, and central portion being of larger transverse cross-sectional area at juncture with said tail portion than at said juncture with said nose portion;

b. said head having a plurality of longitudinally extending cutting grooves formed therein commencing proximate juncture of said nose and central portions and extending rearwardly therefrom;

c. a passageway through said head has first aperture ends defined by open bottoms of at least some of said cutting grooves and terminates in a second aperture end opening onto a surface of said head rearwardly of terminus of said grooves including said first aperture ends.

* * * * *